(12) United States Patent
Palmer

(10) Patent No.: US 10,315,008 B2
(45) Date of Patent: Jun. 11, 2019

(54) PACKAGED URINARY CATHETER WITH CATHETER DISPENSING SYSTEM

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 0 days.

(21) Appl. No.: 16/111,779

(22) Filed: Aug. 24, 2018

(65) Prior Publication Data

US 2019/0046767 A1 Feb. 14, 2019

Related U.S. Application Data

(63) Continuation-in-part of application No. 15/671,341, filed on Aug. 8, 2017.

(51) Int. Cl.
*A61M 25/01* (2006.01)
*A61M 25/00* (2006.01)

(52) U.S. Cl.
CPC ...... *A61M 25/0113* (2013.01); *A61M 25/002* (2013.01); *A61M 25/0136* (2013.01); *A61M 2205/0216* (2013.01)

(58) Field of Classification Search
CPC ............ A61M 25/0113; A61M 25/002; A61M 25/0136; A61M 2205/0216
See application file for complete search history.

(56) References Cited

U.S. PATENT DOCUMENTS

| | | |
|---|---|---|
| 836,303 A | 11/1906 | Christensen |
| 1,206,655 A | 11/1916 | Belcher |
| 2,131,956 A | 10/1938 | Jones |
| 2,221,801 A | 11/1940 | Keppinger |
| 2,422,891 A | 6/1947 | Dickson |
| 2,584,644 A | 2/1952 | Verdi |
| 1,894,119 A | 7/1959 | Stenger |
| 3,365,761 A | 1/1968 | Kalvig |
| 4,140,127 A | 2/1979 | Cianci et al. |
| 4,141,452 A | 2/1979 | Martin et al. |
| 4,230,115 A | 10/1980 | Walz, Jr. et al. |
| 4,451,256 A | 5/1984 | Welkl et al. |
| 4,811,847 A | 3/1989 | Reif et al. |
| 5,108,066 A | 4/1992 | Lundstrom |
| 5,224,681 A | 7/1993 | Lundstrom |
| D358,679 S | 5/1995 | Garrity |
| 5,454,798 A | 10/1995 | Kubalak et al. |
| 5,529,148 A | 6/1996 | O'Laery |
| 5,603,702 A | 2/1997 | Smith et al. |
| 5,690,645 A | 11/1997 | Van Erp |
| 5,993,437 A | 11/1999 | Raoz |
| 6,004,305 A | 12/1999 | Hursman et al. |

(Continued)

*Primary Examiner* — Adam Marcetich
*Assistant Examiner* — Jessica R Arble
(74) *Attorney, Agent, or Firm* — SoCal IP Law Group LLP; Guy Cumberbatch; Steven Sereboff

(57) ABSTRACT

A packaged closed intermittent urinary catheter system equipped with a dispensing system and method of dispensing a packaged catheter using the dispensing system. The dispensing system is a pair of separately translatable movement control devices, each operably engaging the catheter for permitting unidirectional movement of the catheter in a first axial direction relative to the movement control devices.

20 Claims, 22 Drawing Sheets

(56) References Cited

U.S. PATENT DOCUMENTS

| | | | |
|---|---|---|---|
| 6,010,105 | A | 1/2000 | Davis |
| 6,053,905 | A | 4/2000 | Daignault, Jr. et al. |
| 6,179,514 | B1 | 1/2001 | Cheng |
| 6,402,726 | B1 | 6/2002 | Genese |
| 6,427,964 | B1 | 8/2002 | Hillstrom et al. |
| 6,578,709 | B1 | 6/2003 | Kavanagh et al. |
| 7,094,220 | B2 | 8/2006 | Tanghoj et al. |
| 7,458,964 | B2 | 12/2008 | Mosler et al. |
| 7,476,223 | B2 | 1/2009 | McBride |
| 7,985,217 | B2 | 7/2011 | Mosler et al. |
| 9,707,375 | B2 | 7/2017 | Conway et al. |
| 9,782,563 | B2 | 10/2017 | Palmer |
| 9,884,167 | B2 | 2/2018 | Gustavsson |
| 10,099,032 | B2 | 10/2018 | Gustavsson et al. |
| 2003/0050653 | A1 | 3/2003 | Berger |
| 2007/0073222 | A1 | 3/2007 | Lilley Jr. et al. |
| 2007/0088330 | A1 | 4/2007 | House |
| 2008/0103464 | A1* | 5/2008 | Mosler ................. A61M 25/01 604/349 |
| 2012/0168324 | A1 | 7/2012 | Carleo |
| 2012/0239005 | A1 | 9/2012 | Conway et al. |
| 2013/0144271 | A1 | 6/2013 | Passadore et al. |
| 2014/0257250 | A1 | 9/2014 | Palmer |
| 2014/0277333 | A1* | 9/2014 | Lewis ................ A61M 25/0113 623/1.11 |
| 2015/0352324 | A1 | 12/2015 | Palmer |
| 2016/0193443 | A1* | 7/2016 | Palmer .............. A61M 25/0017 206/210 |

* cited by examiner

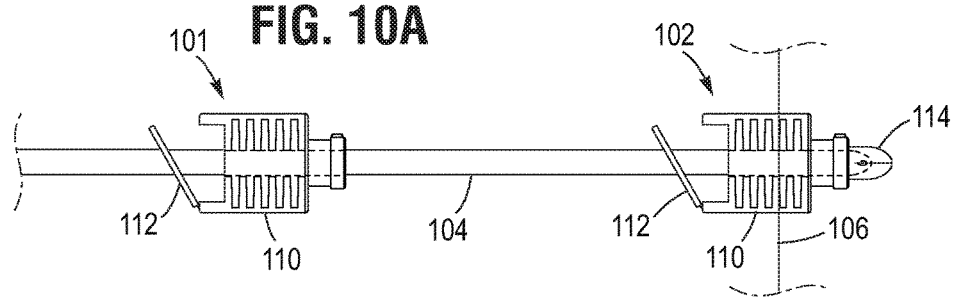
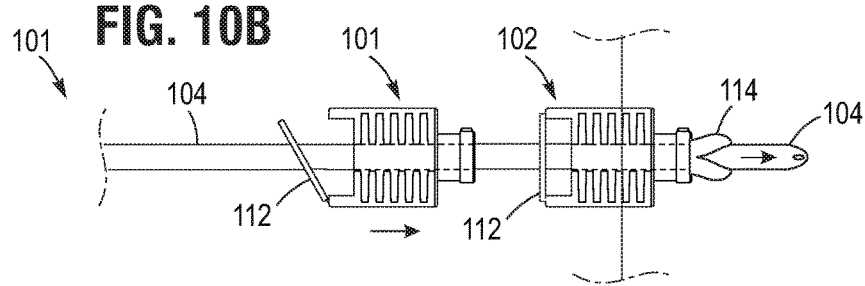
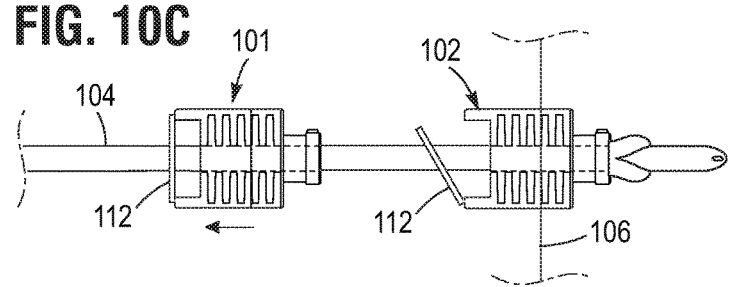
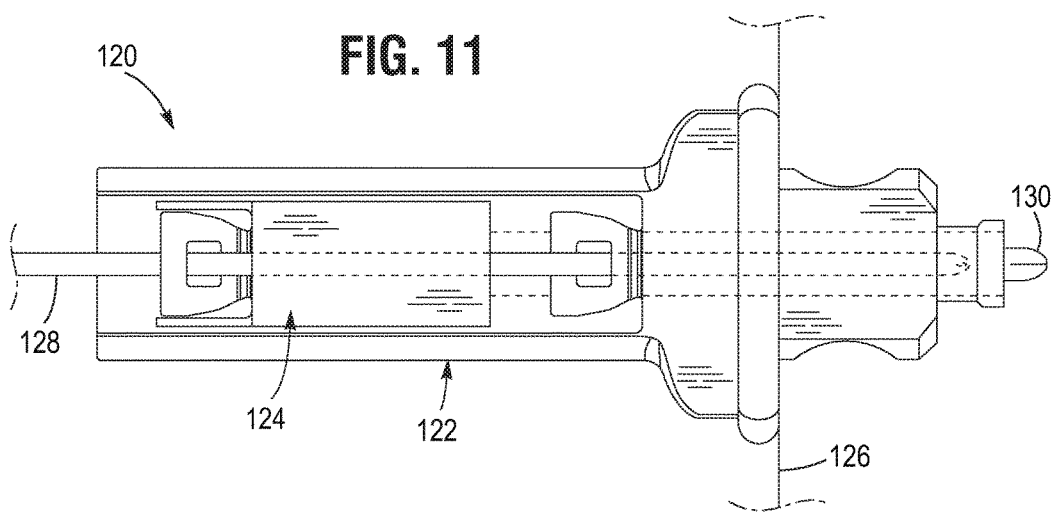

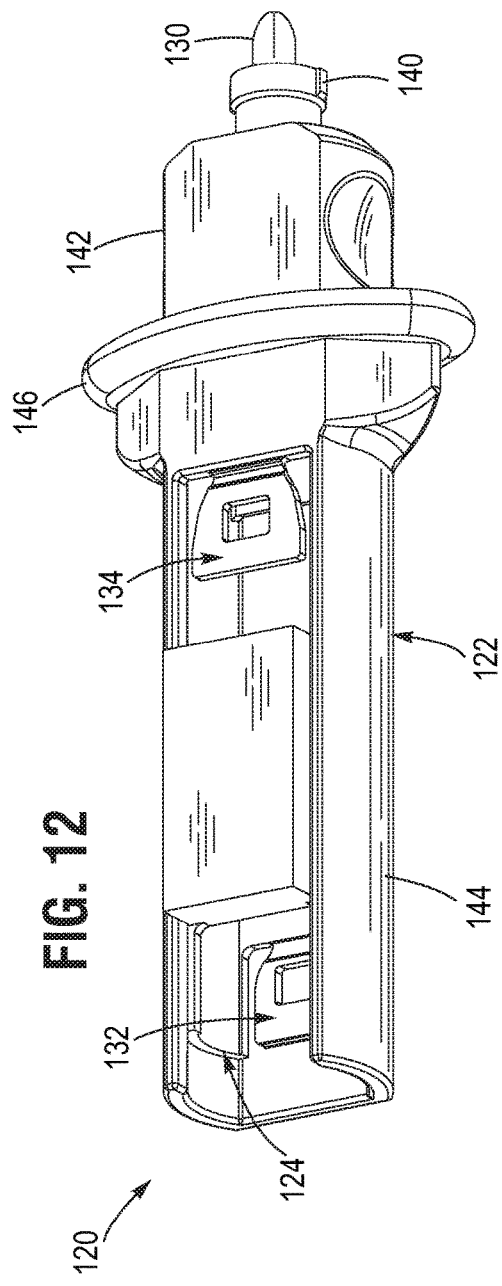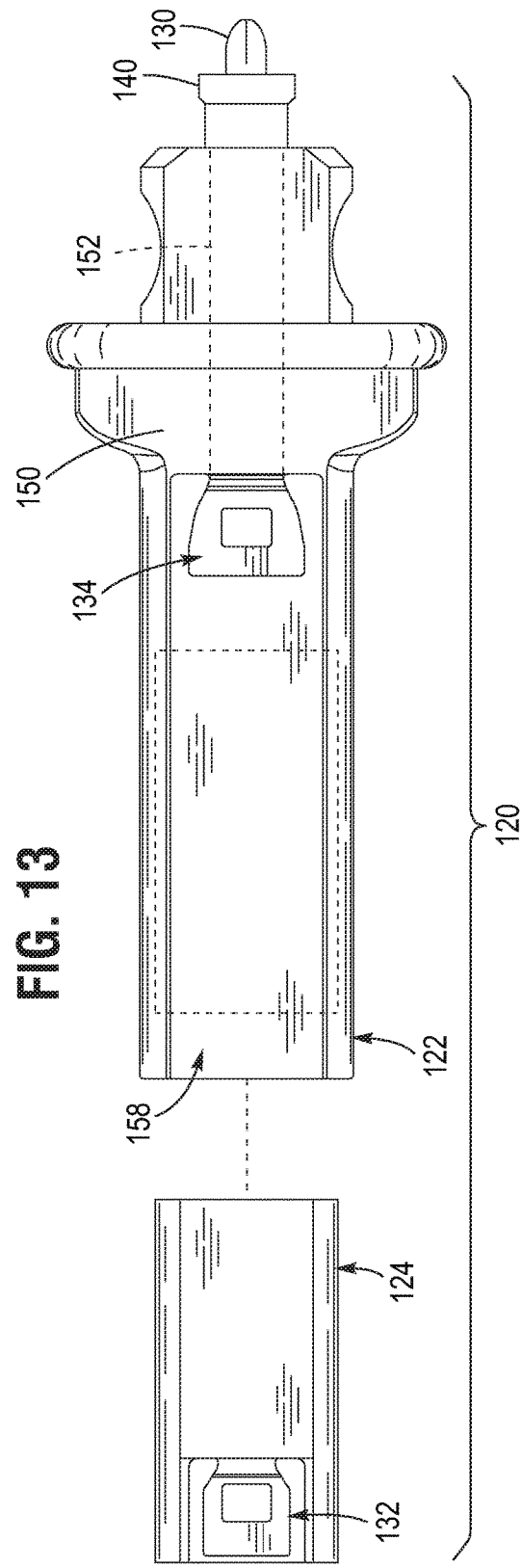

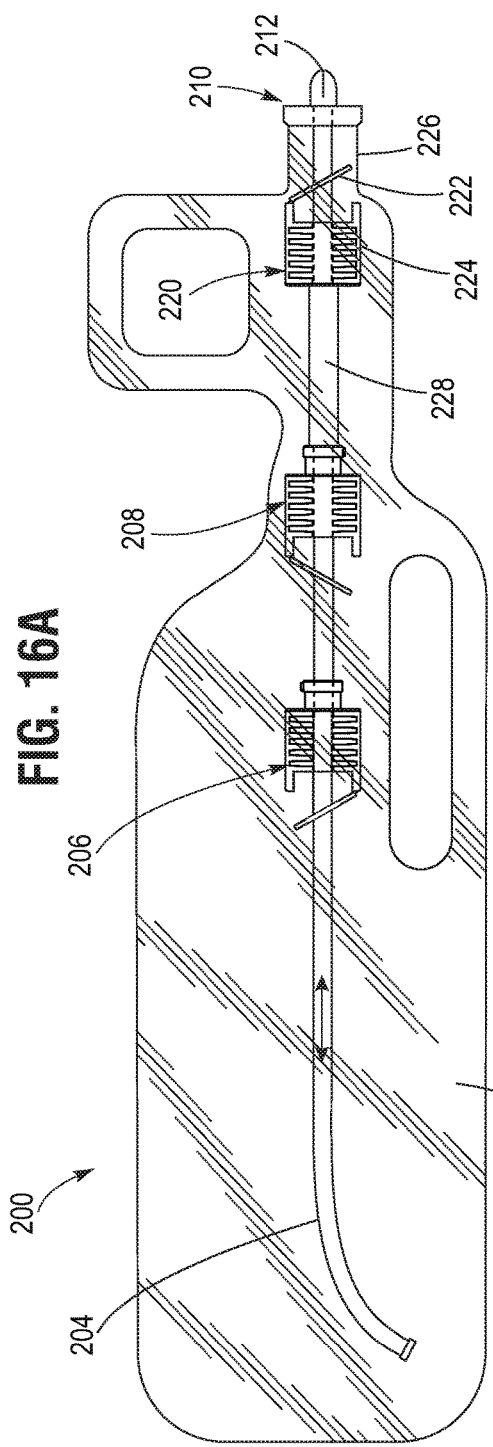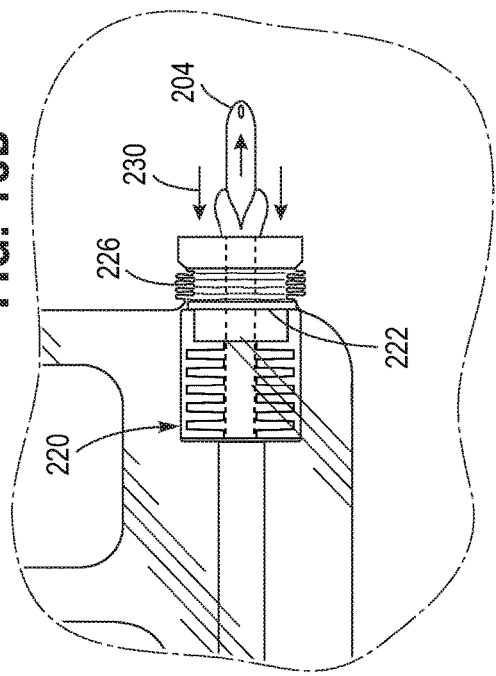

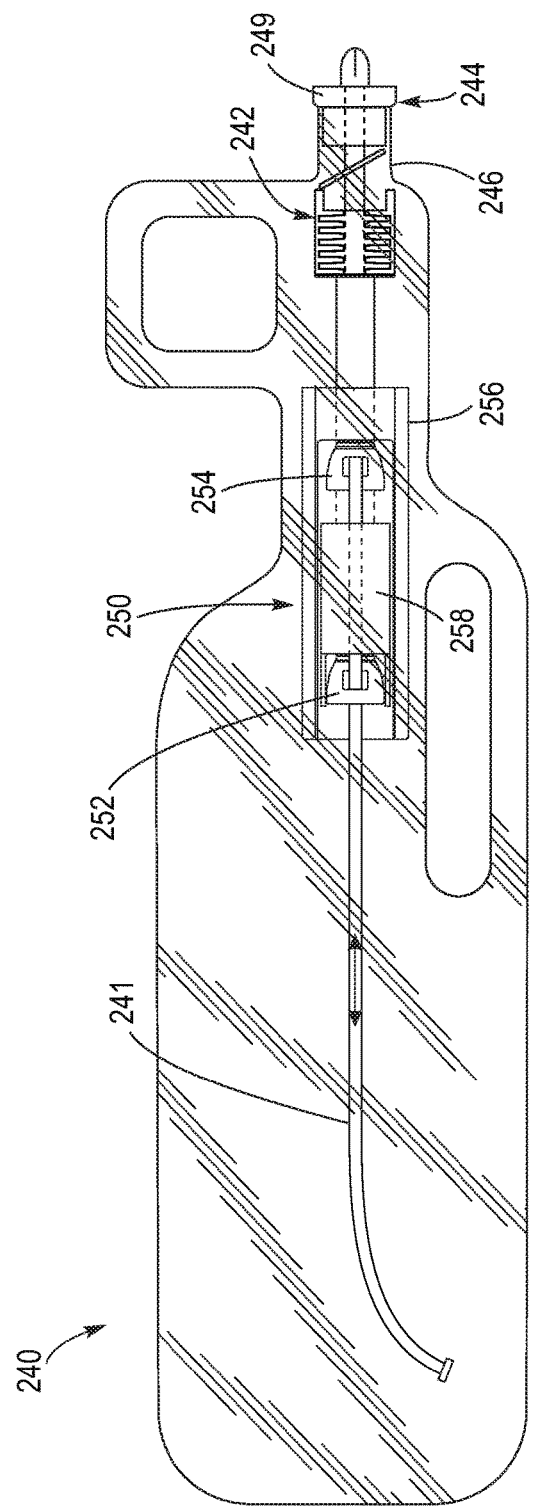
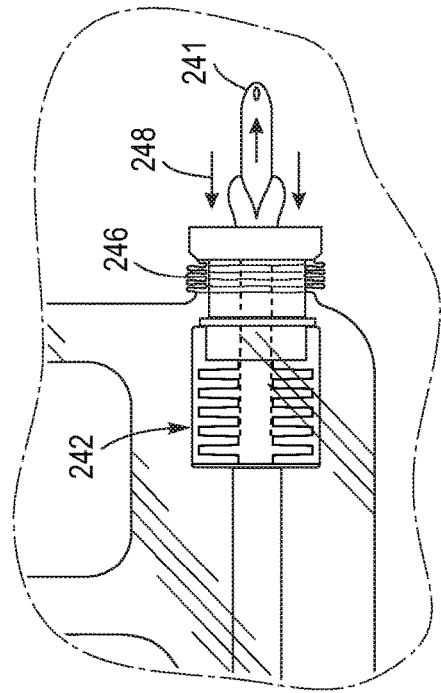
FIG. 17A
FIG. 17B

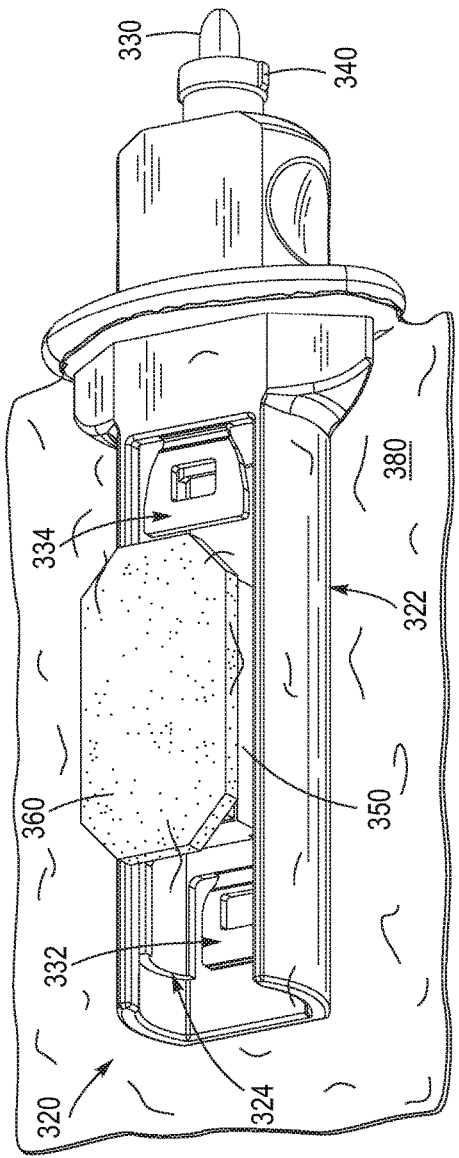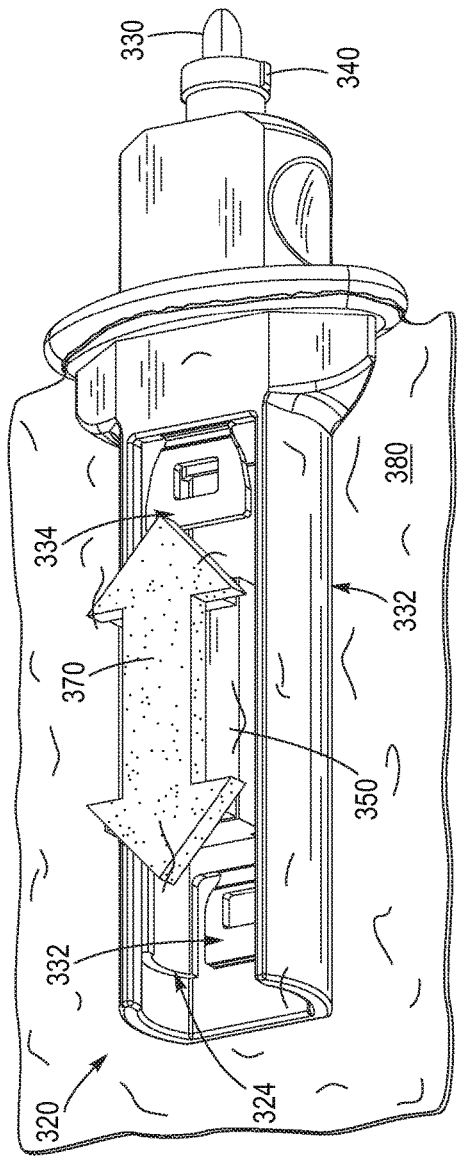

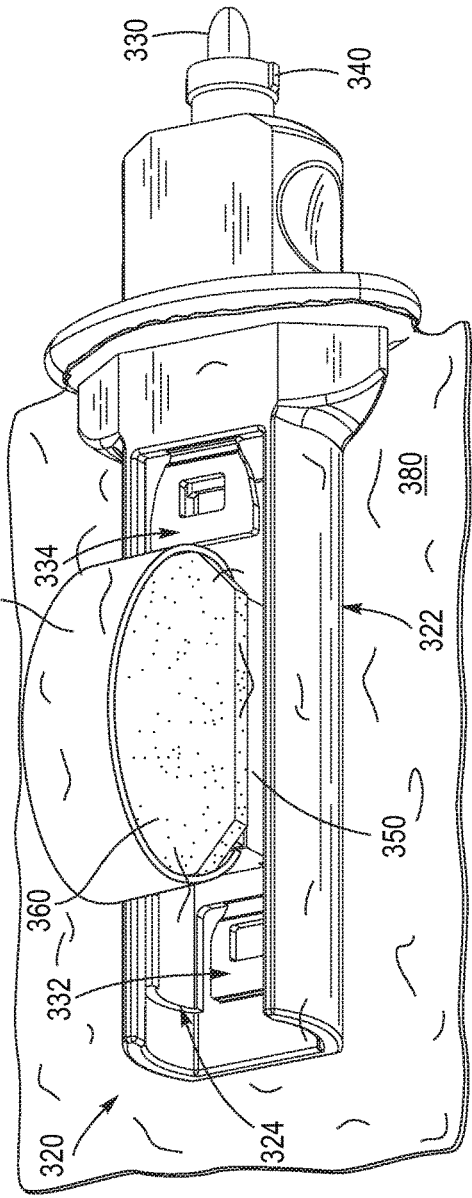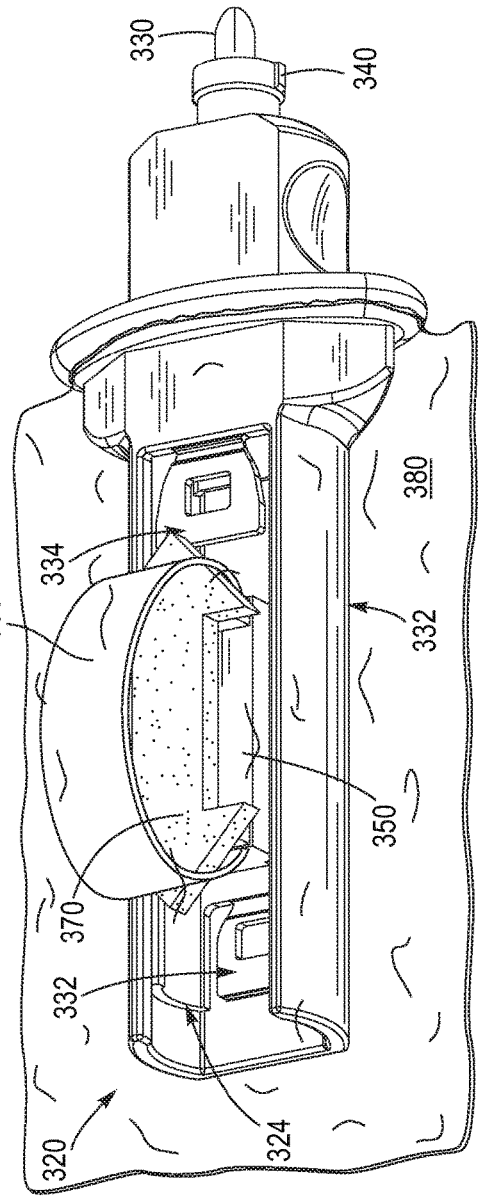

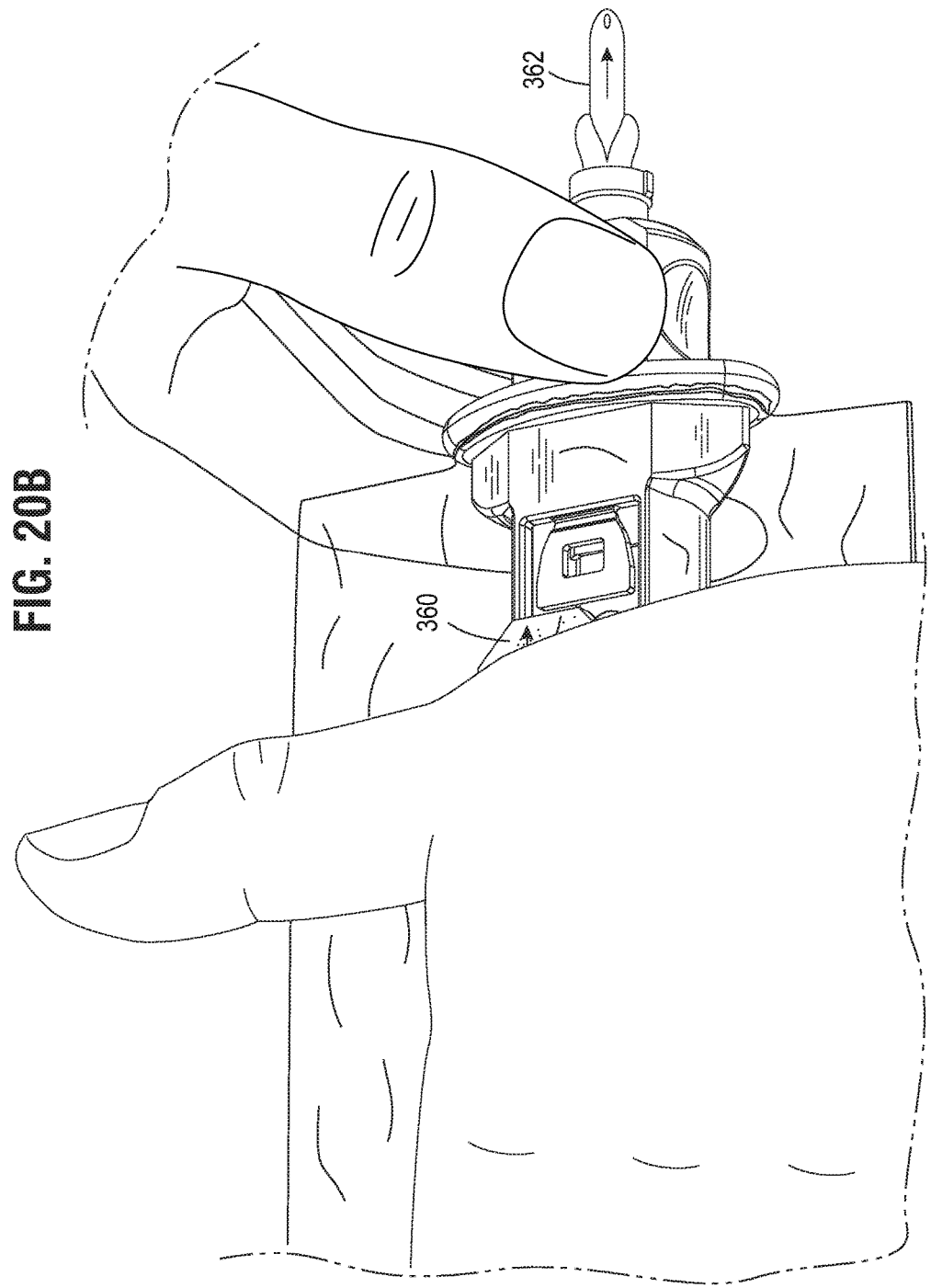

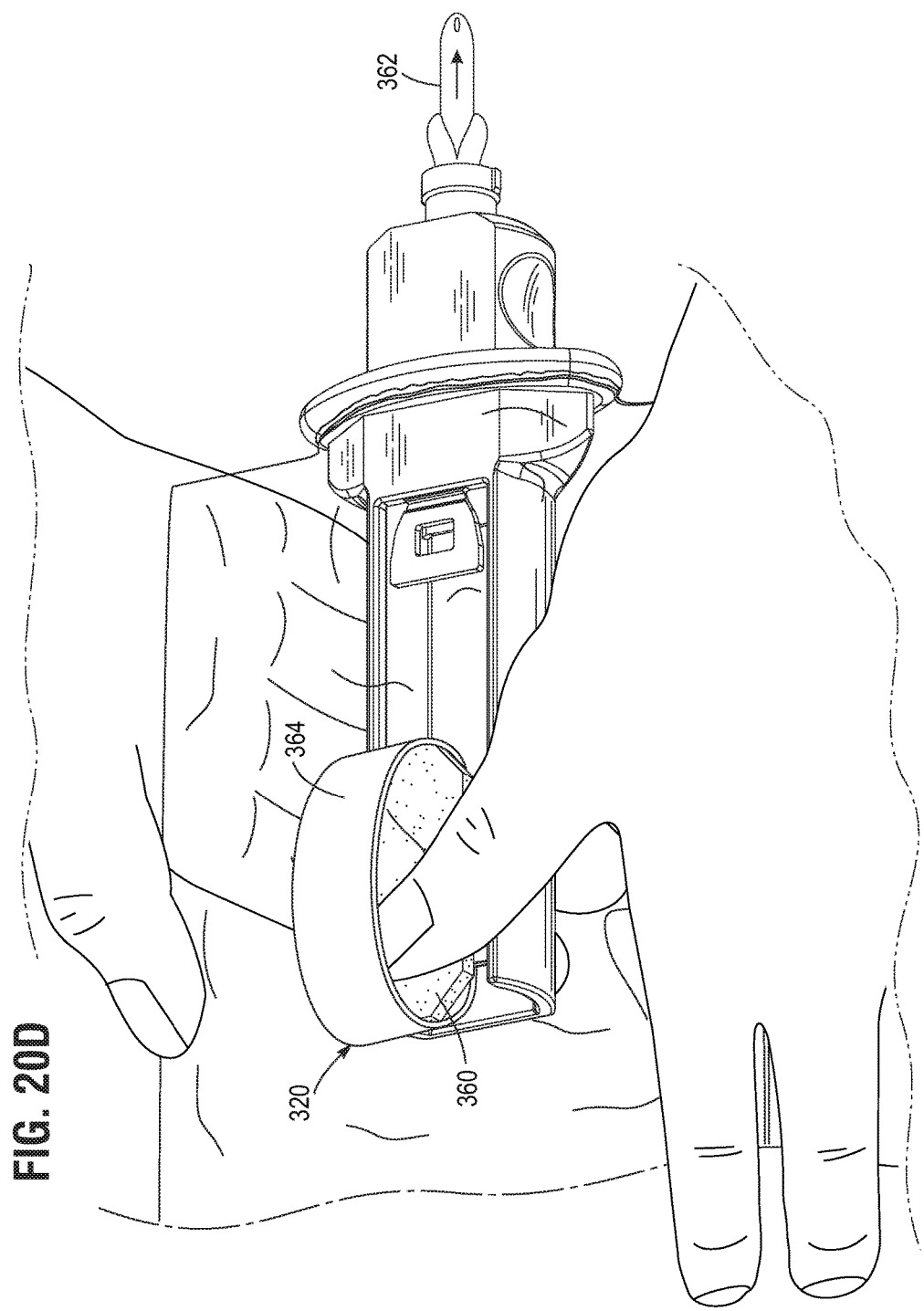

PACKAGED URINARY CATHETER WITH CATHETER DISPENSING SYSTEM

RELATED APPLICATIONS

The present application is a continuation-in-part of co-pending patent application Ser. No. 15/671,341, filed Aug. 8, 2017, the contents of which are expressly incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

The present invention relates to coordinated control devices within a sterile closed intermittent urinary catheter system that facilitate gripping and dispensing of a catheter therein.

BACKGROUND

People with neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. But such continuous catheterization can lead to problems like urinary tract infections (UTI), urethral strictures or male infertility. Intermittent catheterization at regular intervals avoids such negative effects of continuous long term catheterization. Research has shown that intermittent self-catheterization helps reduce urinary tract infections, control urinary leakage (incontinence) and prevent urinary tract damage.

In our highly mobile culture, the ability to have the freedom to leave home for the day or longer is an important part of life. To accommodate this need single use catheters have been developed to allow patients to perform self-catheterization. Urinary catheters are often lubricated to aid in the insertion into a body cavity, thus making the handling of the catheter difficult and messy. Many catheter packages are now designed with the catheter retained in the package. This allows the user to use the package to manipulate the catheter and avoid the messy and possible unsanitary direct contact with the catheter. For instance, a closed system catheter is a self-contained, sterile, pre-lubricated catheter typically housed within a collection bag which eliminates the need to void the urine into a receptacle or toilet as well as the need to hook up any other kind of bag or container. The closed system is also critical for a sterile intermittent catheter insertion technique whereby the catheter is inserted without human touch. However, manipulating a slippery catheter through a plastic bag can be quite difficult even for someone with excellent dexterity. To aid in the manipulation of the catheter various devices have been conceived to assist in movement of the catheter into and out of its package.

For example, U.S. Pat. No. 9,782,563 to Palmer discloses a package including a bag housing a catheter. The catheter passes through a movement control device retained within a housing at the opening of the bag that allows passage of the catheter out of the bag but resists passage back into the bag. Dispensing of a catheter requires the user to hold the movement control device with one hand while using the other hand to grip the lubricated catheter through the bag, typically by pinching the catheter with the thumb and index finger, and pushing the catheter towards and through the movement control device. The one-way valve function of the movement control device thus aids in dispensing of the catheter. Nevertheless, gripping and pushing of a lubricated catheter through the bag is challenging, particularly so for the elderly and the infirm who are the very people who tend to use urinary catheters.

Accordingly, a substantial need continues to exist for a device capable of facilitating and simplifying dispensing of a sterile closed intermittent urinary catheter.

SUMMARY OF THE INVENTION

The present application discloses a sterile closed intermittent urinary catheter system which is an easier to use by virtue of coordinated control devices within the system that facilitates gripping and advancement of a catheter therein.

A first aspect of the invention is a packaged catheter equipped with a dispensing system. A first embodiment of the first aspect of the invention includes (i) packaging defining a product retention chamber, (ii) a catheter defining a longitudinal axis retained within the product retention chamber, and (iii) a pair of separately translatable movement control devices, each operably engaging the catheter for permitting unidirectional movement of the catheter in a first axial direction relative to the movement control devices.

A second embodiment of the first aspect of the invention includes (i) packaging defining a product retention chamber, (ii) a catheter retained within the product retention chamber and defining an insertion end, a fixture end and a longitudinal axis, and (iii) first and second separately translatable movement control devices, each operably engaging the catheter for permitting unidirectional movement of the catheter in a first axial direction relative to the movement control devices, wherein (a) pulling the movement control devices away from one another along the longitudinal axis of the catheter effects longitudinal translation of the first movement control device in a second axial direction opposite the first axial direction along the longitudinal length of the catheter with inconsequential longitudinal translation of the second movement control device along the longitudinal length of the catheter, and (b) pushing the longitudinally separated movement control devices towards one another along the longitudinal axis of the catheter effects longitudinal translation of the second movement control device in the second axial direction along the longitudinal length of the catheter with inconsequential longitudinal translation of the first movement control device along the longitudinal length of the catheter.

The first aspect of the invention can optionally be equipped with a handle grip that includes at least (i) a hand-graspable base member fixedly attached to one of the movement control devices, and (ii) a finger-movable member reciprocally engaged to the base member and fixedly attached to the other movement control device, wherein reciprocation of the movable member relative to the base member effects pulling apart and pushing together of the movement control devices along the longitudinal axis of the catheter so as to effect dispensing of the catheter from the packaging.

A second aspect of the invention is a method of dispensing a catheter from a packaged catheter in accordance with the first aspect of the invention wherein the movement control devices permit unidirectional movement of the catheter in a first axial direction relative to the movement control devices. A first embodiment of the second aspect of the invention includes the steps of (i) pulling the pair of movement control devices away from one another along the longitudinal axis of the catheter so as to effect longitudinal translation of a first movement control device in a second axial direction opposite the first axial direction along the longitudinal length of the catheter with inconsequential longitudinal translation of the second movement control device along the longitudinal length of the catheter, and (ii) pushing the longitudinally separated movement control devices towards one another along the longitudinal axis of the catheter so as to effect longitudinal translation of the second movement control device in the second axial direction along the longitudinal length of the catheter with inconsequential longitudinal translation of the first movement control device along the longitudinal length of the catheter, whereby (iii) pushing of the longitudinally separated movement control devices towards one another along the longitudinal axis of the catheter effects dispensing of the catheter out of the packaging. Stated another way, this involves the second movement control device being held stationary against the patient's anatomy while the first movement control device is moved in the first direction to feed the catheter forward. The first movement control device is then moved in the second direction to get another "bite" of the catheter for feed in.

A second embodiment of the second aspect of the invention pertains to dispensing a catheter from a packaged catheter in accordance with the first aspect of the invention which is equipped with a handle grip, and includes the steps of (i) grasping the base member of the handle grip with a first hand, and (ii) reciprocating the button along a path with a finger on the first hand, wherein (a) movement of the button in one direction along the path effects a pulling movement of the pair of movement control devices away from one another along the longitudinal axis of the catheter so as to effect longitudinal translation of a first movement control device in a second axial direction opposite the first axial direction along the longitudinal length of the catheter with inconsequential longitudinal translation of the second movement control device along the longitudinal length of the catheter, and (b) movement of the button in the other opposite direction along the path effects a pushing movement of the pair of movement control devices towards one another along the longitudinal axis of the catheter so as to effect longitudinal translation of the second movement control device in the second axial direction along the longitudinal length of the catheter with inconsequential longitudinal translation of the first movement control device along the longitudinal length of the catheter, effecting a dispensing of the catheter out of the packaging.

BRIEF DESCRIPTION OF THE DRAWINGS

FIGS. 10A-10C show a pair of movement control devices mounted over a catheter to illustrate a sequence of movement of the catheter using coordinated manipulation of the control members.

FIG. 11 is a plan view of an integrated assembly of a pair of movement control devices mounted within a handle grip component for facilitating single-handed dispensing of the catheter.

FIG. 12 is a perspective view of an integrated assembly of a pair of movement control devices within relatively sliding housings, while FIG. 13 is an exploded plan view thereof.

FIG. 16A is a front view of one embodiment of a packaged catheter having a sterile bag and a pair of movement control devices mounted therein for advancing a catheter, and a safety device in the form of a third movement control device mounted near an outlet that prevents premature distal movement of the catheter from the sterile bag, and FIG. 16B is an enlargement of the outlet showing operation of the safety device.

FIG. 17A is a front view of one embodiment of a packaged catheter having a sterile bag and an integrated assembly of a pair of movement control devices mounted therein for advancing a catheter, as well as a safety device in the form of a third movement control device mounted near an outlet that prevents premature distal movement of the catheter from the sterile bag, and FIG. 17B is an enlargement of the outlet showing operation of the safety device.

FIGS. 19A-19D are perspective views of the integrated assembly of FIG. 18 mounted to an outer panel of a sterile bag with alternative friction-enhancing pads and straps in operative relationship with the finger pad.

FIGS. 20A-20D are perspective views of the integrated assembly of FIGS. 19A and 19C mounted to an outer panel of a sterile bag showing a variety of different ways to grasp and reciprocate the finger pad to advance the catheter from within the bag.

DETAILED DESCRIPTION OF A PREFERRED EMBODIMENT

The present application provides a sterile closed intermittent urinary catheter system which is easier to use by virtue of coordinated control devices within a sterile bag that facilitates gripping for advancement and retrieval of the catheter from the collection bag. The catheter is advanced by hand through manipulation from outside the sterile bag.

Nomenclature

10 Packaged Catheter
20 Packaging
21 First Longitudinal End of Packaging
22 Second Longitudinal End of Packaging
29 Product Retention Chamber
30 Dispensing System
31 First Movement Control Device
32 Second Movement Control Device
40 Main Body of Each Movement Control Device
401 First Portion of Main Body of Each Movement Control Device
402 Second Portion of Main Body of Each Movement Control Device
40LA Longitudinal Axis of Main Body
41 First Longitudinal End of Main Body
42 Second Longitudinal End of Main Body
43 Engagement Members
431 First Longitudinally Extending Engagement Member
432 Second Longitudinally Extending Engagement Member
45 Cap or Seal snap fit on the Main Body to hold the soft silicone introducer tip in place at the exit
49 Passageway Through Main Body
49i Interior End (Opening) of Passageway Through Main Body
49e Exterior End (Opening) of Passageway Through Main Body
49CA Central Axis of Passageway
50 Locking Member of Each Movement Control Device
51 First or One Lateral End of Locking Member
52 Second or Other Lateral End of Locking Member
55 Hinge
55P Hinge Pivot Axis
59 Orifice Though Locking Member
59CA Central Axis of Orifice
60 Catheter
61 Lumen or Insertion End
62 Funnel or Fixture End
69CA Longitudinal Central Axis of Catheter
69x1 First Axial Longitudinal Direction
69x2 Second Axial Longitudinal Direction
70 Handle Grip
71 Base Member of Handle Grip
72 Activation Element or Button on Handle Grip
72p Path of Movement of Activation Element or Button
80 Release Actuator Element
90 Handle Opening in Packaging
X Longitudinal Direction
Y Lateral Direction
Z Transverse Direction Definitions As utilized herein, including the claims, the term "inconsequential," when used to describe longitudinal translation of a movement control device along the longitudinal length of a catheter, means a distance of less than 1 cm.

Construction

Figure 1:
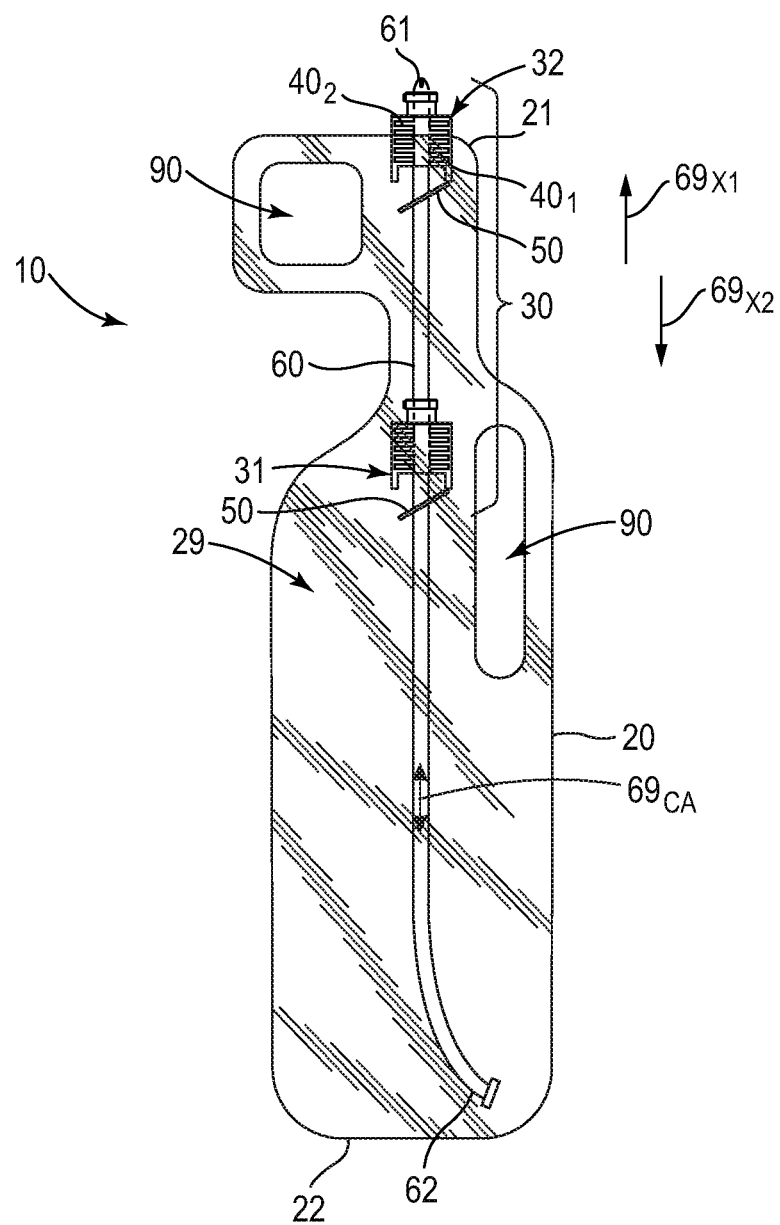
FIG. 1 is a front view of one embodiment of a packaged catheter in accordance with this invention, depicting an assembly of a pair of movement control members of a dispensing system pulled apart in a longitudinally spaced relationship and the catheter fully retained within the packaging.
Figure 2:
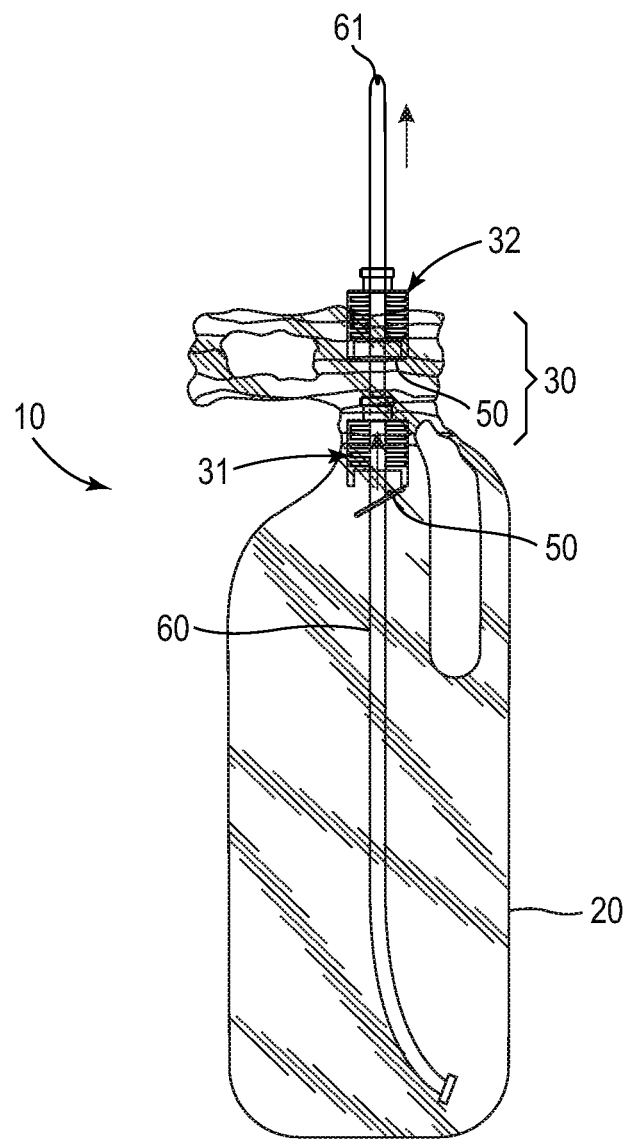
FIG. 2 is a front view of the invention depicted in FIG. 1 depicting the movement control devices of the dispensing system pushed together and the catheter partially dispensed from the packaging.

Referring to FIGS. 1 and 2, the invention is a packaged catheter 10 equipped with a dispensing system 30.

Packaged Catheter

The packaged catheter 10 includes a catheter 60, such as an intermittent urinary catheter, retained within the product retention chamber 29 of a package 20. The catheter 60 defines an insertion end 61 and a fixture end 62, and a longitudinal central axis 69CA. Consistent with similar devices, advancement of the catheter 60 into the urethra occurs in a distal direction and retraction in a proximal direction. Therefore, the insertion end 61 is the distal end and the fixture end 62 is the proximal end.

Catheter

The catheter 60 may have any desired longitudinal length and shape effective for achieving the function of eliminating urine from the bladder of a male or female patient. Preferably, the longitudinal length for an adult female catheter 60 is between 2-6 inches, the longitudinal length of the adult male catheter 60 is between 10-16 inches, and the longitudinal length of a pediatric catheter 60 is between 5-11 inches.

Packaging

The packaging 20 may be selected from any of the customary packaging used for catheters so long as the packaging is sufficiently supple and flexible that the packaging 20 does not prevent or inhibit translation of the movement control devices (31 and 32) towards and away from one another when gripped through the packaging 20. In a preferred embodiment, the packaging 20 is in the form of a polymer bag sealed around its exterior edges and around any handle openings therein. The packaging 20 will thus be referred to as a bag from now on, but one of skill in the art will understand that alternative packaging solutions are possible. For instance, the term "bag" implies a closed end, while the packaging used in the catheter system disclosed herein may not be closed, and may instead define a drain line therethrough.

Dispensing System

The dispensing system 30 includes a pair of movement control devices (31 and 32) for facilitating longitudinal x movement of the catheter 60 from a second longitudinal end 22 of the bag 20 towards a first longitudinal end 21 of the bag 20 for controlled dispensing of the catheter 60 from the bag 20.

The movement control devices (31 and 32) each operably engage the catheter 60 and are separately translatable along the longitudinal central axis 69CA of the catheter 60 to cause unidirectional movement of the catheter 60 in a first axial direction 69x1 (distally) relative to the movement control devices (31 and 32). More particularly, and as will be explained below, each movement control device (31 and 32) is constructed so as to automatically be able to freely slide along the longitudinal length of the catheter 60 in a second axial direction 69x2, but is automatically unable to freely slide along the catheter 60 in the first axial direction 69x1.

The unidirectional nature of the movement control devices (31 and 32), allows a user to quickly, easily and controllably dispense a catheter 60 from a bag 20 by repetitively pushing together and pulling apart the paired set of movement control devices (31 and 32). In a preferred embodiment, an outer movement control device 32 is secured to the first longitudinal end 21 of the bag 20 and may be partially exposed out of the first longitudinal end 21, while the inner movement control device 31 is contained within the bag 20. In the configuration of FIG. 1, the inner movement control device 31 is spaced apart from the outer movement control device 32, while in FIG. 2 the inner movement control device 31 has been pushed towards the outer movement control device 32. The catheter 60 is pushed by the inner movement control device 31 which resists relative movement of the catheter therethrough in the second axial direction 69x2, but the catheter slides easily in the first axial direction 69x1 (distally) through the outer movement control device 32. Subsequently, the inner movement control device 31 may be displaced longitudinally over the catheter 60 in the second axial direction 69x2 (proximally) and away from the outer movement control device 32, back into the position shown in FIG. 1.

To summarize, pushing the longitudinally separated movement control devices (31 and 32) towards one another along the catheter 60 effects longitudinal translation of the second movement control device 32 in the second axial direction 69x2 with inconsequential longitudinal translation of the first movement control device 31 along the catheter 60. Conversely, pulling the movement control devices (31 and 32) away from one another along the longitudinal length of the catheter 60 effects longitudinal translation of the first movement control device 31 along the catheter 60 in the second axial direction 69x2 with inconsequential longitudinal translation of the second movement control device 32 along the catheter 60. Stated another way, displacing the inner movement control device 31 in a distal direction relative to the second movement control device 32 advances the catheter 60, and retracting the inner movement control device 31 in a proximal direction relative to the second movement control device 32 resets the inner control device 31 to its initial position without moving the catheter 60.

A further explanation and illustration of the coordinated manipulation of a paired set of movement control devices is provided below in the context of FIGS. 10A-10C.

Movement Control Device

FIGS. 1-9, and in particular FIGS. 3-7, depict a preferred embodiment of the movement control devices 31, 32.

This embodiment of the movement control device 31, 32 has a main body 40 and a locking member 50 hingedly attached to the main body 40. The main body 40 and locking member 50 are preferably formed as a monolithic device with the locking member 50 pivoting about a living hinge 55 formed in the single piece device. The locking member 40 may be made from any suitable material, including various plastics such as polyethylene, polypropylene, polyvinyl chloride (PVC), and nylon.

Figure 4:
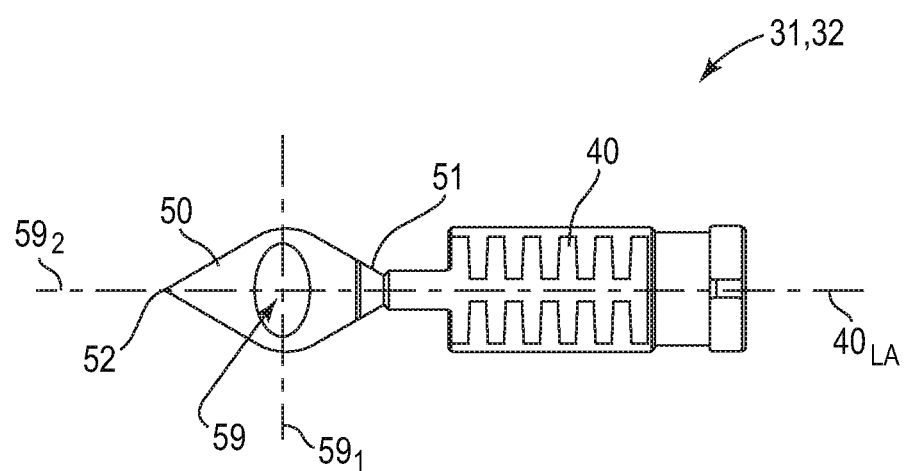
FIG. 4 is a side view of the catheter movement control device depicted in FIG. 3.
Figure 5:
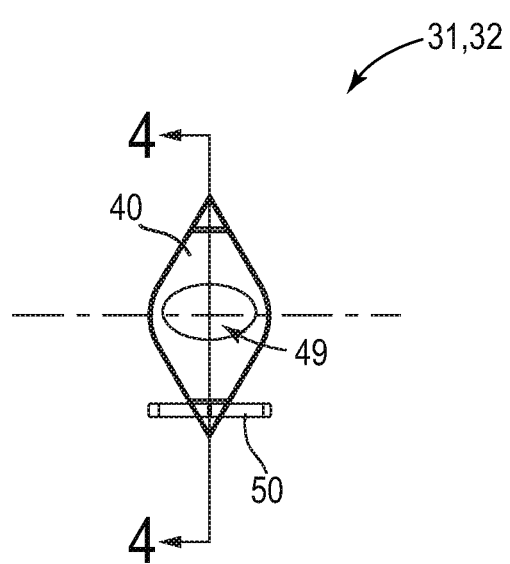
FIG. 5 is an end view of the catheter movement control device depicted in FIG. 3.
Figure 6:
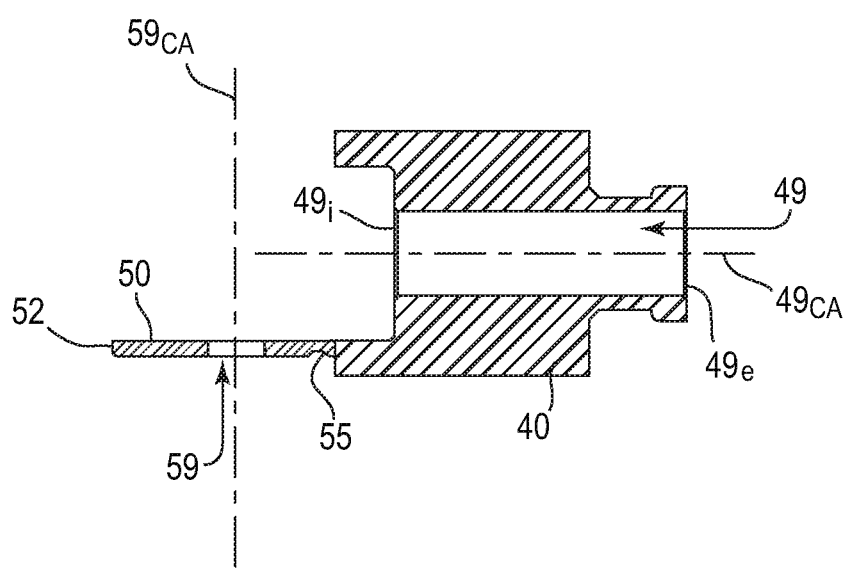
FIG. 6 is a cross-sectional side view of the catheter movement control device depicted in FIG. 3 taken along line 6-6.

The main body 40 of the movement control device 31, 32 has a first longitudinal end 41 and a second longitudinal end 42, and defines a longitudinal axis 40LA (FIG. 4). A passageway 49 extends through the main body 40 from an opening 49i in the first longitudinal end 41 of the main body 40 to an opening 49e in the second longitudinal end 42 of the main body 40. The passageway 49 is preferably linear and defines a central axis 49CA (FIG. 6). The passageway 49 is sized and configured to allow passage of the lumen portion of a catheter 60.

Figure 7:
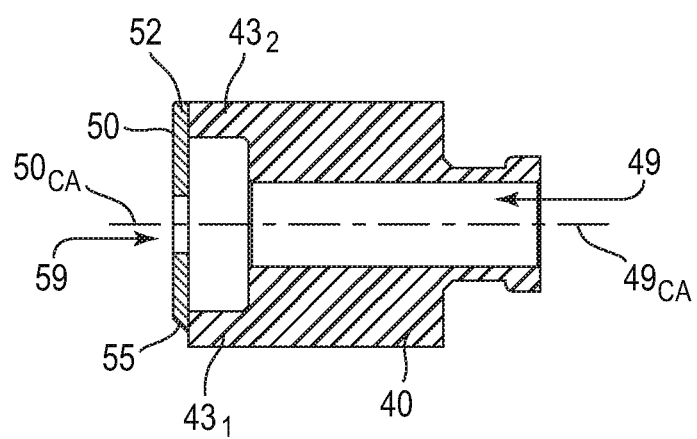
FIG. 7 is a cross-sectional side view of the catheter movement control device depicted in FIG. 3 taken along line 7-7, but with the locking mechanism pivoted into a first dispensing position.

A first lateral end 51 of the locking member 50 hingedly attaches to the main body 40 at hinge 55, permitting pivoting of the locking member 50 relative to the main body 40 about a hinge pivot axis 55p between a first aligned position depicted in FIG. 7, and a second misaligned position depicted in FIGS. 3-6. In the first aligned position the second lateral end 52 of the locking member 50 contacts the main body 40 and the central axis 59CA of an orifice 59 through the locking member 50 is aligned with the central axis 49CA of the passageway 49. When in the first aligned position a catheter 60 may be axially translated through the aligned orifice 59 and passageway 49. Pivoting of the locking member 50 from the first aligned position towards the second misaligned position pivots the second lateral end 52 of the locking member 50 away from the main body 40, resulting in an increasing misalignment of the central axis 59CA of the orifice 59 and the central axis 49CA of the passageway 49 until movement of a catheter 60 is inhibited through the misaligned orifice 59 and passageway 49. Stated another way, friction between the catheter 60 and the orifice 59 pivots the locking member 50 away from the main body 40 into an angled position such that the catheter binds within the orifice 59 and is prevented from moving farther.

In a preferred embodiment, laterally y spaced engagement members 43 extend longitudinally x from a longitudinal end of the main body 40, with a first lateral end 51 of the locking member 50 hingedly attached to a first engagement member $43_1$ at hinge 55, and the second engagement member $43_2$ located to contact the second lateral end 52 of the locking member 50 when the locking member 50 is in the first aligned position. The engagement members 43 provide a modest offset between the passageway 49 and the orifice 59 for avoiding severe bending and kinking of the catheter 60 when the central axis 59CA of the orifice 59 and the central axis 49CA of the passageway 49 are misaligned.

Pivoting of the locking member 50 about the hinge pivot axis 55p is effected by axial translation of the movement control device 31, 32 along the longitudinal length of a catheter 60 passing through the passageway 49 and frictionally passing through the orifice 59 in the movement control device 31, 32. Referring generally to FIGS. 1 and 2, axial translation of a movement control device 31, 32 in the first longitudinal direction 69x1 along the length of a catheter 60 causes pivoting of the locking member 50 towards the second misaligned position so as to lock the movement control device 31, 32 onto the catheter 60. When locked, any further movement of the movement control device 31, 32 in the first longitudinal direction 69x1 will effect concomitant movement of the catheter 60 along with the movement control device 31, 32 in the first longitudinal direction 69x1. In other words, the movement control device 31, 32 pushes the catheter 60.

In contrast, axial translation of a movement control device 31, 32 in the second longitudinal direction 69x2 along the length of a catheter 60 causes pivoting of the locking member 50 towards the first aligned position so as to unlock the movement control device 31, 32 from the catheter 60. When unlocked, the movement control device 31, 32 is free to travel along the longitudinal length of the catheter 60. Such freedom of travel can continue along the entire length of the catheter 60 in the second longitudinal direction 69x2, but will of course be promptly lost when the movement control device 31, 32 is moved in the first longitudinal direction 69x1 as the locking member 50 will pivot into the second misaligned position and lock the movement control device 31, 32 onto the catheter 60.

It should be noted that the friction between the catheter 60 and the orifice 59 of each movement control device 31, 32 occurs any time there is relative movement therebetween; i.e., automatically. Therefore, if the catheter 60 slides distally through the orifice 59 it contacts the inner edges of the orifice and causes the locking member 50 to pivot to an aligned unlocked position, whereas when the catheter 60 slides proximally through the orifice 59 it almost immediately causes the locking member 50 to pivot to a misaligned or locked position which binds on the catheter 60. In other words, the catheter 60 may be advanced through each movement control device 31, 32 but cannot be retracted. However, provision may be made to bypass the locking member 50 by including a latch or some other physical impediment to its free movement; such as latching the locking member 50 in an unlocked position. In one example, a release actuator element 80 is shown in and described with respect to FIG. 9.

The size and dimensions of the movement control device 31, 32 are generally dictated by the size of the catheter 60 with which it is used, but the main body 40 should be large enough to be retentively pinched between the thumb and index finger in order to allow dispensing of the catheter 60 from the bag 20 through the movement control device 31, 32. Dimensions of an exemplary movement control device 31, 32 are provided in Table One below.

TABLE ONE (Exemplary Dimensions)

| DIMENSION | SIZE |
| --- | --- |
| Longitudinal Length of Main Body 40 | 25 mm |
| Lateral Width of Main Body 40 | 20 mm |
| Transverse Depth of Main Body 40 | 10 mm |
| Cross Sectional Area of Passageway 49 | 200 mm$^2$ |
| Thickness of Locking Member 50 | 1-2 mm |
| Cross Sectional Area of Orifice 59 | 100 mm$^2$ |

Referring again to FIGS. 1 and 2, at least one of the movement control devices 31 and 32 is preferably fixedly attached to the bag 20 when incorporated into a packaged catheter 10. Namely, a first portion 40$_1$ of the main body 40 of the outer movement control device 32 is positioned within the product retention chamber 29 defined by the bag 20, and a second portion 40$_2$ of the main body 40 is positioned exterior to the product retention chamber 29. The passageway 49 through the main body 40 of the movement control device 32 provides a port through the bag 20 from an interior end 49$i$ of the passageway 49 to an exterior end 49$e$ of the passageway 49. The affixed movement control device 32 can conveniently be heat sealed at a longitudinal end 21 of the bag 20.

Figure 3:
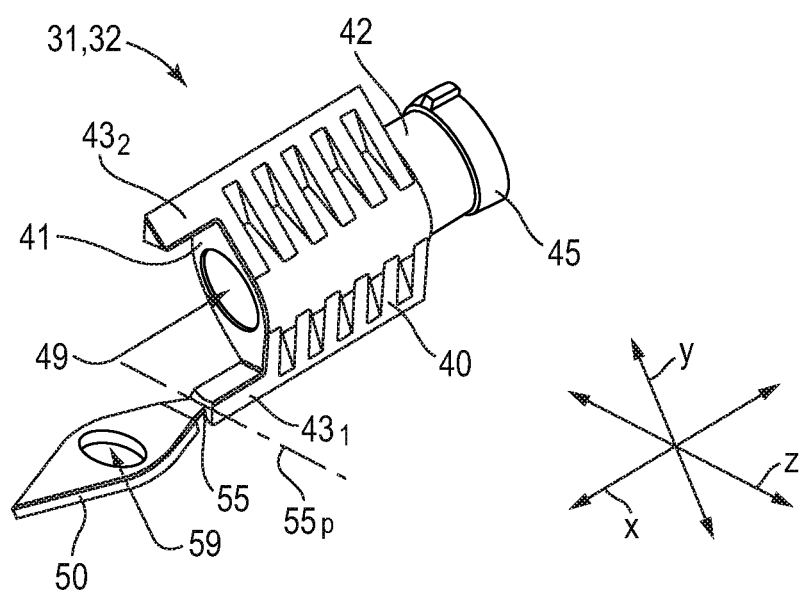
FIG. 3 is a perspective view of one of the movement control devices depicted in FIGS. 1 and 2 with the locking member pivoted into the second locking position.

As seen in FIG. 3, a cap or seal 45 can be placed over the exterior end 49$e$ of the passageway 49 to maintain sterility prior to usage. The inner movement control device 31 is preferably wholly located within the product retention chamber 29 of the bag 20 and may also be fixedly attached to the bag 20 so long as the bag 20 is supple enough to allow the movement control devices 31 and 32 to be pushed together and pulled apart.

Figure 8:
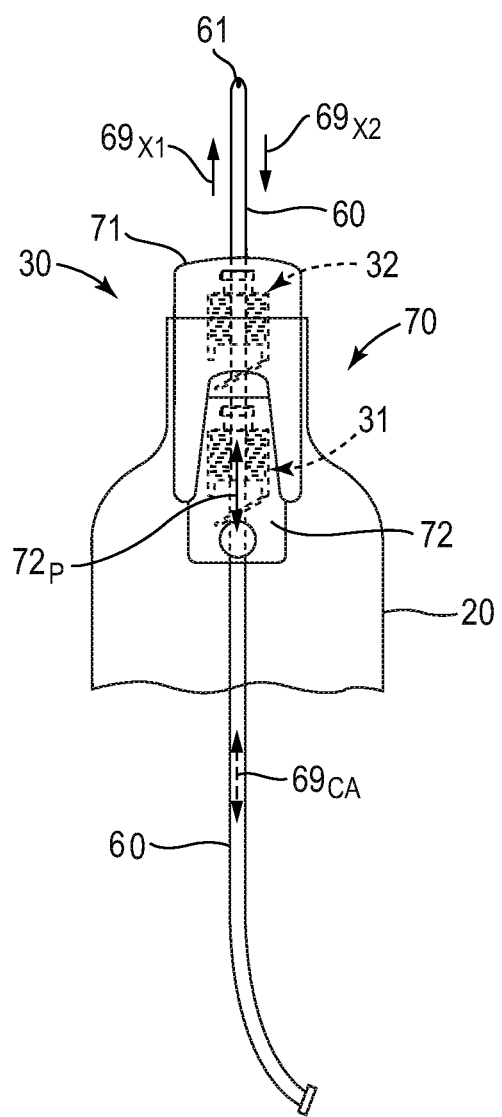
FIG. 8 is a front view of a portion of another embodiment of a packaged catheter in accordance with this invention schematically depicting a handle grip component for facilitating single-handed dispensing of the catheter.

The dispensing system 30 may further include a handle grip 70 as seen in FIG. 8 for facilitating single-handled dispensing of the catheter 60 from the bag 20 using the dispensing system 30, a feature long sought by users.

FIG. 8 schematically depicts the handle grip 70 having a hand-graspable base member 71, and a finger-movable member 72 reciprocally (i.e., telescopically) engaged to the base member 71 for travel along a path 72$p$ relative to the base member 71. The base member 71 and movable member 72 are preferably sized, configured and arranged for thumb actuation of the movable member 72 while cradling of the base member 71 within the palm of that hand. Of course, the term "finger-movable" implies that the member 72 is movable by a finger, thumb, fist, wrist or any other part of the hand or arm, as well as by using intermediate inanimate objects. The base member 71 is fixedly attached to a second outer one of the movement control devices 32, while the movable member 72 is fixedly attached to a first inner one of the movement control devices 31, whereby reciprocation of the movable member 72 relative to the base member 71 along a path 72$p$ effects a pulling apart and pushing together of the movement control devices 31 and 32 along the longitudinal axis 69CA of the catheter 60 so as to effect dispensing of the catheter 60 from the bag 20.

The finger-movable member 72 may optionally be biased, such as by use of a spring, towards the pushed apart configuration to effect auto "reloading" of the dispensing system 30. When the dispensing system 30 includes a handle grip 70, the bag 20 can be conveniently heat sealed to the base member 71 with the movable member 72 retained wholly within and actuated through the bag 20.

Figure 9:
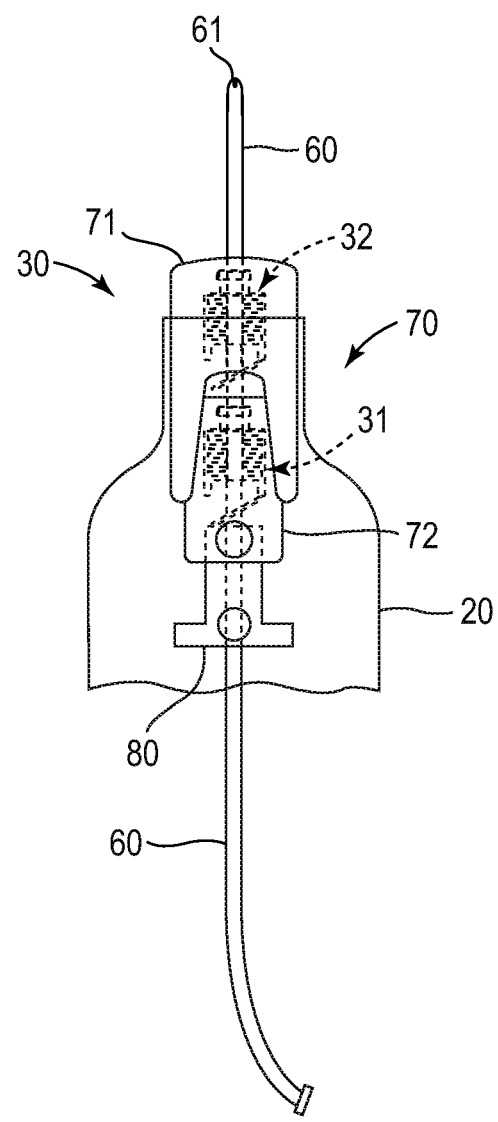
FIG. 9 is a front view of a portion of the handle grip component schematically depicted in FIG. 8, further equipped with a schematically depicted release element.

Referring to FIG. 9, a release actuator element 80 may optionally be provided for effecting selective manual sustained pivoting of the locking member 50 on the first movement control device 31 into the aligned position regardless of real-time longitudinal movement of the catheter 60 relative to the first movement control device 31. This permits movement of a dispensed catheter 60 in the second axial longitudinal direction 69$x$2 (i.e., retraction) relative to the first movement control device 31. Specifically, actuating the release actuator element 80 while at the same time pushing the first movement control device 31 against the second movement control device 32 to pivot its locking member 50 into the aligned position enables retraction of the catheter 60 back into the bag 20. At the same time, the release actuator element 80 also pushes the first movement control device 31 against the locking member 50 of the second movement control device 32, thus holding the second locking member open to allow free movement through both movement control devices.

The release actuator element 80 may be telescopingly mounted onto the movable member 72 for travel between a first disengaged position and a second engaged position. In the disengaged position, the release actuator element 80 is spaced from the locking member 50 on the first movement control device 31, while in the engaged position the release actuator element 80 contacts and pivots the locking member 50 on the first movement control device 31 into an aligned positioned.

Use

The packaged intermittent urinary catheter 10 can be used by patients for self-catheterization. Prior to use the patient should take all sanitary procedures advised by their doctors to decrease the risks of infection.

Referring to the embodiment depicted in FIGS. 1 and 2, first the seal or cap 45 is removed to open the port through the bag 20 defined by the passageway 49 through the main body 40 of the second movement control device 32.

The user then grasps or pinches the main body 40 of the first or inner movement control device 31 through the bag 20 with one hand, grasps or pinches the main body 40 of the second or outer movement control device 32 with the other hand through the bag 20, and then repetitively pushes together and pulls apart the movement control devices 31 and 32 as depicted in FIGS. 1 and 2. As mentioned, pulling the two movement control devices 31 and 32 apart "loads" the dispensing system 30 without expelling the catheter 60 from the bag 20, and pushing the movement control devices 31 and 32 together dispenses a length of the catheter 60 from the bag 20.

A clearer depiction of this "inchworm" sort of catheter advancement is seen in FIGS. 10A-10C where a first or inner movement control device 101 and a second or outer movement control device 102 are shown mounted over a catheter 104. The first and second movement control devices 101, 102 may be identical to that shown in FIGS. 3-7. By "mounted over" the catheter 104 is meant that the catheter passes through the longitudinal passageway through the main body 110 and the orifice though the locking member 112 of each movement control device 101, 102. A symbolic line 106 is drawn to represent an outer edge of the sterile bag within which the catheter 104 is stored.

FIG. 10A is a resting position with the catheter 104 stored within the sterile bag 106 and preferably inside of a bullet-shaped introducer tip 114 mounted to an exterior end of the outer movement control device 102. The introducer tip 114 is sized to fit within the outer end of the urethra and made of a flexible elastomer which has petals that the catheter 104 spreads apart upon passage therethrough. When the user wishes to utilize the catheter, the bag 106 is first brought into proximity with the genitals, and the introducer tip 114 inserted into the tip of the urethra. The introducer tip 114 helps prevent any bacteria that may be around the urethra opening from contacting the catheter 104, which in turn helps reduce instances of infection.

Next, the user holds the outer movement control device 102 steady through the bag 106 and grasps and advances it toward the inner movement control device 101, as in FIG. 10B. Friction between the catheter 104 and the orifice though the locking member 112 of the inner movement control device 101 pivots the locking member away from the main body 110 to about a 45° angle as shown. This misaligns the orifice though the locking member 112 with the catheter axis and causes the catheter 104 to be pushed along by the inner movement control device 101. The catheter 104 emerges from the petals of the introducer tip 114 into the outer end of the urethra. Friction between the catheter 104 and the orifice though the locking member 112 of the outer movement control device 102 forces the locking member to pivot toward and eventually contact the main body 110, which aligns the orifice though the locking member 112 with the catheter axis and permits catheter movement.

Finally, FIG. 10C shows leftward movement of the inner movement control device 101 over the catheter 104 which pivots its locking member 112 against the main body 110, aligns the orifice though the locking member with the catheter axis and permits movement thereover. The locking member 112 of the outer movement control device 102 is slightly pulled by the catheter 106 to the angled, misaligned position shown, which creates friction on the catheter and prevents it from being retracted farther back into the bag 106. Repeating the steps shown in FIGS. 10B and 10C gradually inches the catheter 104 out of the sterile bag 106 and through the urethra of the user to the desired location where urine flows.

Referring to FIGS. 1 and 2, two-handed pushing and pulling of the movement control devices 31 and 32 to effect dispensing of a catheter 60 may be simplified by attaching both movement control devices 31 and 32 to the bag 20 in longitudinally spaced relationship and providing a handle opening 90 proximate each movement control device 31 and 32.

The dispensing system 30 also functions to preventing the fixture end 62 of the catheter 60 from advancing out of the bag 20.

Referring to the embodiment depicted in FIGS. 8 and 9, the user cradles the base member 71 in the palm of a hand with the fingers wrapped around and gripping the base member 71 and the thumb of that same hand placed upon a pad on the activation element 72. The user then uses the thumb to reciprocate the activation element 72 relative to the base member 71 along the path of travel 72p, thereby pulling the movement control devices 31 and 32 apart and loading the system. Subsequently, pushing the movement control devices 31 and 32 together dispenses a length of the catheter 60 from the bag 20 when the activation element 72 is moved in the opposite direction along the path 72p.

Still referring to FIGS. 8 and 9, one-handed pushing and pulling of the movement control devices 31 and 32 to effect dispensing of a catheter 60 may be simplified by including the handle grip 70 feature.

Alternative Embodiments

In addition to the previously-described movement control devices and handle grips integrating the same, the applicants have developed further alternatives for use in sterile closed intermittent urinary catheter systems, as explained below.

FIG. 11 is a plan view of an integrated assembly 120 of a pair of movement control devices mounted within a handle grip for facilitating single-handed dispensing of the catheter. With specific reference to FIGS. 12-15, the integrated assembly 120 includes a larger base member 122 and a smaller movable member 124 arranged to move within the base member. The base member 122 is desirably secured to one end of a sterile bag, as schematically shown at 126 in FIG. 11, and defines an exterior handle grip of the integrated assembly 120. A catheter 128 passes longitudinally through the assembly 120 and typically is positioned with its distal tip just inside of an introducer tip 130 in a stored position.

Greater detail of the integrated assembly 120 is shown in FIGS. 12-15, but FIG. 11 depicts the sterile bag 126 at the same placement as the sterile bag 106 in FIGS. 10A-10C as well as a pair of movement control devices 132, 134 within the assembly. A first or inner movement control device 132 forms a part of the movable member 124 while a second or outer movement control device 134 forms a part of the base member 122. It will be understood that relative displacement of the movement control devices 132, 134 advances the catheter 128 in the "inchworm" manner depicted in FIGS. 10A-10C.

With reference now to the detailed views of FIGS. 12-15, the larger base member 122 includes a distal hub 140 from which the introducer tip 130 projects. The hub 140 in turn is molded together with an ergonomic external handle 142 and an internal housing 144 which are separated by a flange 146. When assembled with the sterile bag 126, the handle 142 is outside while the housing 144 is inside, with the bag 126 preferably adhered or heat sealed to the exterior of the flange 146, as seen in FIG. 11. The integrated assembly 120 has a generally rectangular lateral cross-section which presents a flat non-rotating profile inside the bag to help the user apply pressure from both sides.

The internal housing 144 includes a relatively wide distal end 150 completely surrounding a lumen 152 therethrough, shown in FIG. 13, that also passes through the external handle 142 and distal hub 140 for passage of the catheter 128. On its proximal end, the housing 144 includes an elongated chute that extends into the bag 126. The chute is closed on three sides by a floor 154 and two sidewalls 156 that are slightly concave on their inner faces. The chute defines a longitudinal slightly oval channel 158 therein for reciprocal movement of the movable member 124. The movable member 124 is shown within the channel 158 in FIG. 12 and exploded therefrom in FIG. 14, with an outline thereof in phantom the channel 158.

Figure 15A:
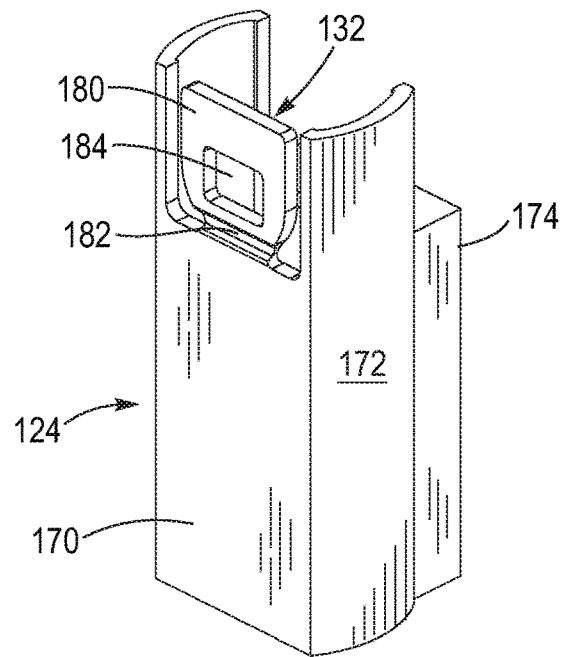
Figure 15B:
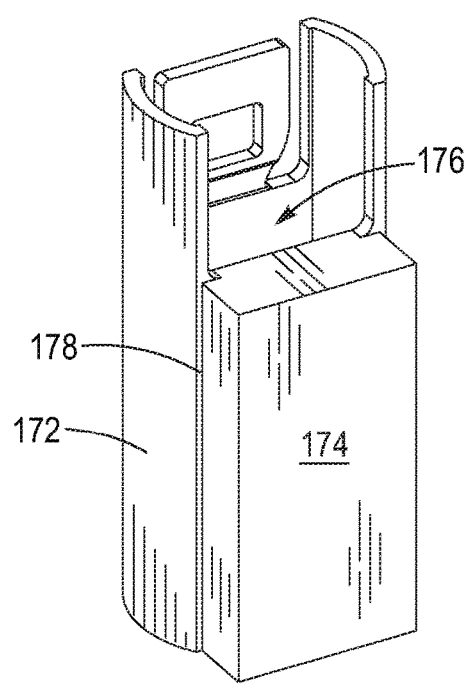
Figure 15C:
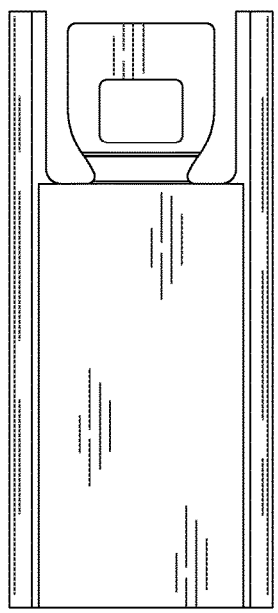
Figure 15D:
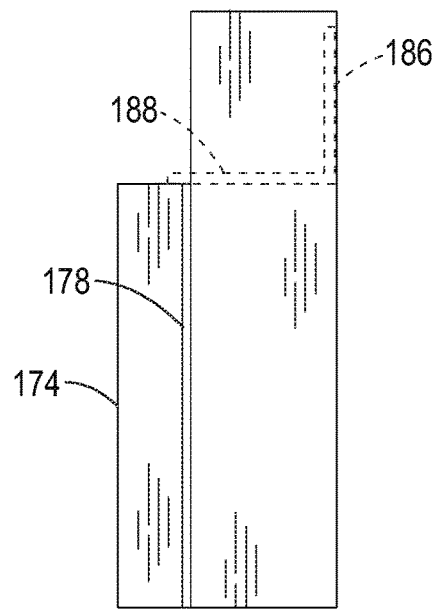

The second or outer movement control device 134 comprises a cantilevered tab 160 connected to one side of the wide distal end 150 at a hinge 162, preferably a living hinge. Instead of a discrete main body, as with the movement control devices described above, the rest of the base member 122 serves as the main body. The tab 160 has an orifice 164 therethrough that serves to alternately slide over or catch on the catheter 128. The tab 160 generally bends from the longitudinally-aligned position 166 as shown in FIGS. 12 and 15D down into the channel 158 into engagement with the catheter 128 and to a misaligned position 168 angled about 90° from longitudinal.

As seen in FIGS. 14A-14D, the movable member 124 has a generally tubular housing formed by a floor 170, two sidewalls 172 and an upper finger pad 174. The two sidewalls 172 are slightly outwardly convex so as to closely fit within the slightly oval channel 158 defined by the chute of the base member 122. The housing defines a longitudinal throughbore 176 for passage of the catheter 128. The upper finger pad 174 is separated from the two sidewalls 172 by a pair of outwardly-directed longitudinal grooves 178 whose purpose will be explained below.

Figure 14A:
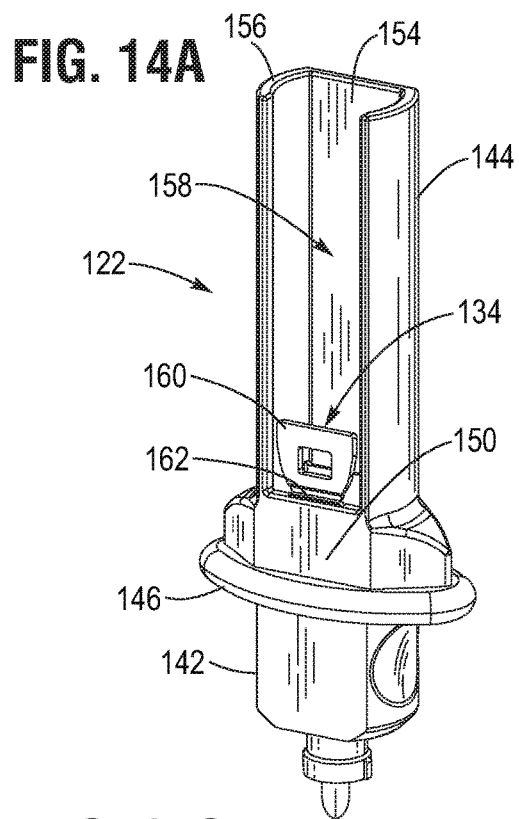
FIGS. 14A-14D are various views of an outer base member that forms a part of the integrated assembly of FIG. 12, and FIGS. 15A-15D are various views of a smaller movable member that slides within the base member.
Figure 14B:
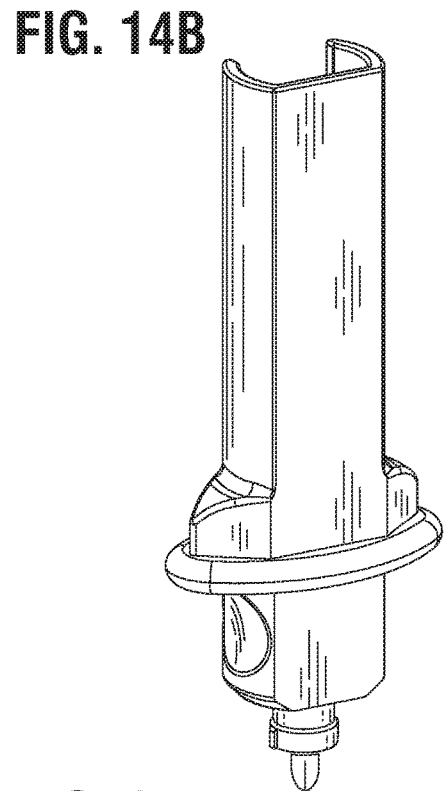
Figure 14C:
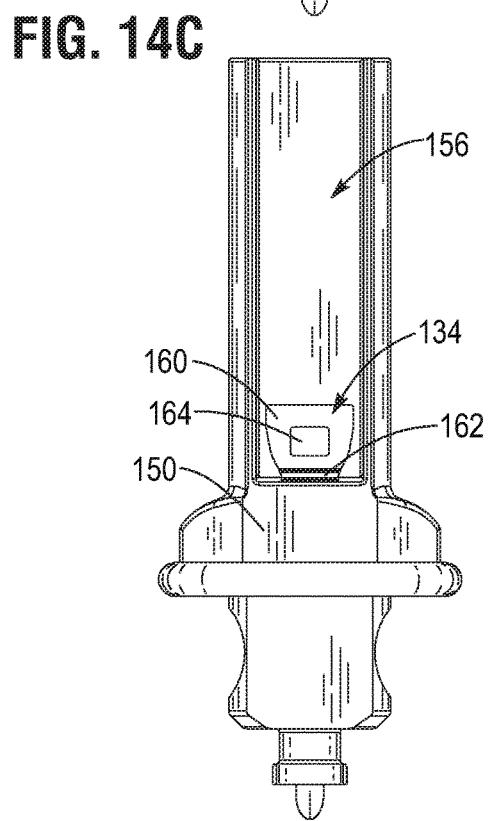
Figure 14D:
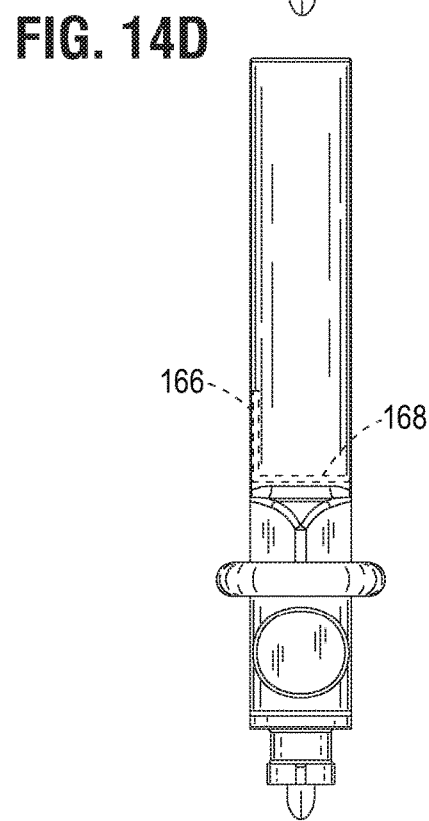

The first or inner movement control device 132 comprises a cantilevered tab 180 connected to the floor 170 at one side of the generally tubular housing with a hinge 182, preferably a living hinge. Instead of a discrete main body, as with the movement control devices described above, the rest of the movable member 124 serves as the main body. The tab 180 has an orifice 184 therethrough that serves to alternately slide over or catch on the catheter 128. The tab 180 generally bends from the longitudinally-aligned position 186 as shown in FIGS. 12 and 14D up into the throughbore 176 into engagement with the catheter 128 and to a misaligned position 188 angled about 90° from longitudinal. As seen best in FIG. 14B, the finger pad 174 terminates short of the two sidewalls 172 so that the tab 180 contacts one end of the finger pad 174 when in the misaligned position 188.

Now with reference back to FIGS. 12 and 13, the movable member 124 fits closely within the slightly oval channel 158 defined by the chute of the base member 122, with the first or inner movement control device 132 on an end opposite the second or outer movement control device 134. The outwardly-directed longitudinal grooves 178 flanking the upper finger pad 174 receive longitudinal edges of the two sidewalls 156 on the chute of the base member 122 so that the movable member 124 is held and guide thereby.

To assemble the sterile closed intermittent urinary catheter system, the movable member 124 is first inserted into the oval channel 158 of the base member 122. Next, the two tabs 160, 180 forming the movement control devices 132, 134 are bent so that they extend across the respective passageways defined by the base member 122 and the movable member 124. Once bent, the catheter 128 may pass through the orifices 164, 184 of the tabs 160, 180 and positioned with its distal tip just inside the introducer tip 130, as seen in FIG. 11. The outer sterile bag 126 may be formed around the assembly 120, preferably after positioning of the catheter 128 therein.

When assembled, the user may easily manipulate the finger pad 174 through the flexible plastic of the bag 126 while simultaneously holding still the base member 122, such as by grasping the ergonomic external handle 142. This operation may even be done with one hand. To help move the finger pad 174, rubber tape or other such friction-inducing material may be added to the exterior of the bag over the pad, and various other solutions are disclosed herein. The generally rectangular lateral cross-section of the integrated assembly 320 aids in these various movements by presenting resistance to rotation about the longitudinal axis and also a flatter profile for the user to compress between his or her hands.

Feed Lock

In addition to facilitating advancement of a catheter from a closed intermittent urinary catheter system, the present application also discloses a safety measure to help prevent premature expulsion of the catheter from the sterile bag. As with most such systems, once an outer packaging is removed, the catheter may be advanced. If the user has not yet positioned and inserted an introducer tip into the urethra, there is the possibility that the catheter may be prematurely advanced and then come into contact with the exterior of the urethra, an area with many germs. If the user inadvertently picks up bacteria from outside the urethra and transfers it into the urethra, an infection may ensue.

FIG. 16 illustrates a system of a sterile catheter package 200 having a flexible bag 202 defining a reservoir therein and containing a catheter 204 and a dispensing system with a first movement control device 206 and a second movement control device 208. The package 200 and first and second movement control devices 206, 208 are as described above, with the latter facilitating advancement of the catheter 204 from within the reservoir and out through an outlet 210 which may include an introducer tip 212.

The system further includes a safety device in the form of a third movement control device 220 mounted over the catheter 204 adjacent its distal tip. Unlike the other two, the orientation of the third movement control device 220 is reversed with a locking tab 222 located on a distal side of a main body 224. The third movement control device 220 is mounted close to the outlet 210 and in particular just inside a collapsible extension 226 of the bag 202. The locking tab 222 has an orifice through which the catheter 204 extends and when the catheter 204 is displaced distally relative to the third movement control device 220 it tends to pivot the locking tab 222 away from the main body 224 such that the orifice becomes misaligned with the catheter axis—the locked position. Thus, in the configuration shown in FIG. 16 the third movement control device 220 prevents distal movement of the catheter 204 and thus prevents the catheter from being dispensed from within the bag 202.

To operate the system, the user first inserts the introducer tip 212 into the urethra and applies pressure by manipulating the bag 202 such as with its handles. This pressure produces a reaction force from the urethra opening, indicated by the force arrows 230 in FIG. 16A, which collapses the extension 226 of the bag 202. Contact of the collapsing extension 226 pivots the locking tab 222 toward or against the main body 224 such that the orifice becomes aligned with the catheter axis—the unlocked position. At this stage, manual coordinated movement of the first and second movement control devices 206, 208 by grasping through the bag 202 advances the catheter 204 from within the bag. Since the catheter 204 emerges directly into the urethra by virtue of the pre-inserted introducer tip 212, no bacteria is carried into the urethra.

FIG. 17A is a front view of another embodiment of a packaged catheter 240 having a catheter 241 housed within a sterile bag with an outlet end 244. As with the sterile catheter package 200, a safety device in the form of a movement control device 242 mounts within the sterile bag close to the outlet 244, and in particular just inside a collapsible extension 246 of the bag. The movement control device 242 works in the same manner as described above. FIG. 17B shows collapse of the extension 246 of the bag from reaction pressure 248 against the urethra such that the movement control device 242 opens or unlocks and the catheter 241 may be advanced. In this embodiment, the outlet 244 features a solid cap member 249 having an inwardly-extending tubular portion that contacts the locking tab of the movement control device 242.

The packaged catheter 240 also has an integrated assembly 250 of a pair of movement control devices 252, 254 mounted therein for advancing a catheter. The integrated assembly 250 may be the same as the integrated assembly 120 described above with respect to FIG. 11, and includes a larger base member 256 and a smaller movable member 258 arranged to slide within the base member. The smaller movable member 258 has a finger pad on its front surface that may be manipulated through the flexible bag, or the finger pad may be adhered to an inner side of the outer wall of the bag. Reciprocal sliding of the movable member 258 within the base member 256 advances the catheter 241 out of the outlet 244 of the sterile bag.

Figure 18:
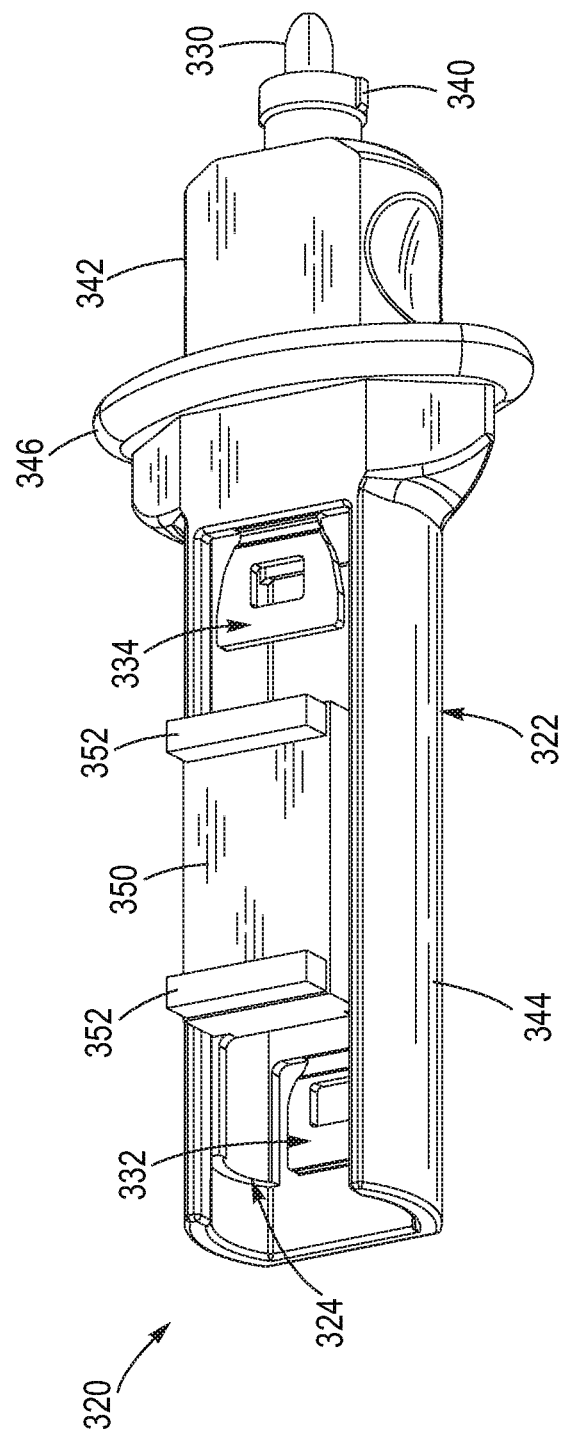
FIG. 18 is a perspective view of an integrated assembly of a pair of movement control devices within relatively sliding housings having an alternative finger pad.

FIG. 18 is a perspective view of an integrated assembly 320 of a pair of movement control devices within relatively sliding housings which is similar to the integrated assembly 120 described above within respect to FIG. 12. The integrated assembly 320 includes a larger base member 322 and a smaller movable member 324 arranged to move within the base member. The base member 322 may be secured to one end of a sterile bag, such as schematically shown at 126 in FIG. 11, and defines an exterior handle grip of the integrated assembly 320. A catheter (not shown) passes longitudinally through the assembly 320 and typically is positioned with its distal tip just inside of an introducer tip 330 in a stored position.

A first or inner movement control device 332 forms a part of the movable member 324 while a second or outer movement control device 334 forms a part of the base member 322. It will be understood that relative displacement of the movement control devices 332, 334 advances the catheter in the "inchworm" manner depicted in FIGS. 10A-10C.

As in the detailed views of the prior embodiment of FIGS. 12-15, the larger base member 322 includes a distal hub 340 from which the introducer tip 330 projects. The hub 340 in turn is preferably molded together with an ergonomic external handle 342 and an internal housing 344 which are separated by a flange 346. When assembled with the sterile bag, the handle 342 is outside while the housing 344 is inside, with the bag preferably adhered or heat sealed to the exterior of the flange 346, such as seen in FIG. 11.

The movable member 324 has a generally tubular housing topped by an upper finger pad 350. The upper finger pad 350 has an alternative configuration than flat as shown, with two spaced apart and laterally-extending raised bars 352 on an upper surface. The bars 352 in conjunction with the recessed area therebetween facilitates purchase of a person's finger, thumb, or other portion of the hand or arm when sliding the movable member 124 back-and-forth through the bag. That is, the bars 352 project upward and thus form an easy-to-manipulate finger pad 350. Of course, other such projections upward from a flat finger pad may be used, such as an "X" pattern or the like. The finger pad 350 is manipulated by the user through the flexible bag, and may also be adhered to an inner surface of the bag to avoid slippage therebetween.

FIGS. 19A and 19B are perspective views of the integrated assembly 320 of FIG. 18 mounted to a sterile bag with alternative friction-enhancing pads 360, 370 in operative relationship with the finger pad 350. The friction-enhancing pads 360, 370 are desirably adhered to an outer panel 380 of the bag directly over the finger pad 350. The friction-enhancing pad 360 of FIG. 19A has a six-sided polygonal shape which maximizes surface area over the finger pad 350, while the friction-enhancing pad 370 of FIG. 19B has a double-headed arrow shape to indicate the direction of sliding movement. Alternatively, a double-headed arrow may be printed onto the polygonal friction-enhancing pad 360. The friction-enhancing pads 360, 370 may be made of various compressible materials, such as rubber, closed-cell foam, or the like, or may be formed of a plastic with friction-enhancing features provided on the upper surface, such as bumps, ribs, a gritty layer, or others. Preferably the friction-enhancing pads 360, 370 are flexible to conform to the bag and assist the user in transmitting force to the underlying finger pad 350. As before, the finger pad 350 may be adhered to an inner surface of the bag to avoid slippage therebetween.

FIGS. 19C and 19D are perspective views of the integrated assembly 320 of FIG. 18 mounted to a sterile bag with the alternative friction-enhancing pads 360, 370 supplemented with loops or straps 364, 366. The straps 364, 366 may be used to help a user grasp and linearly reciprocate the finger pad 350.

Figure 20A:
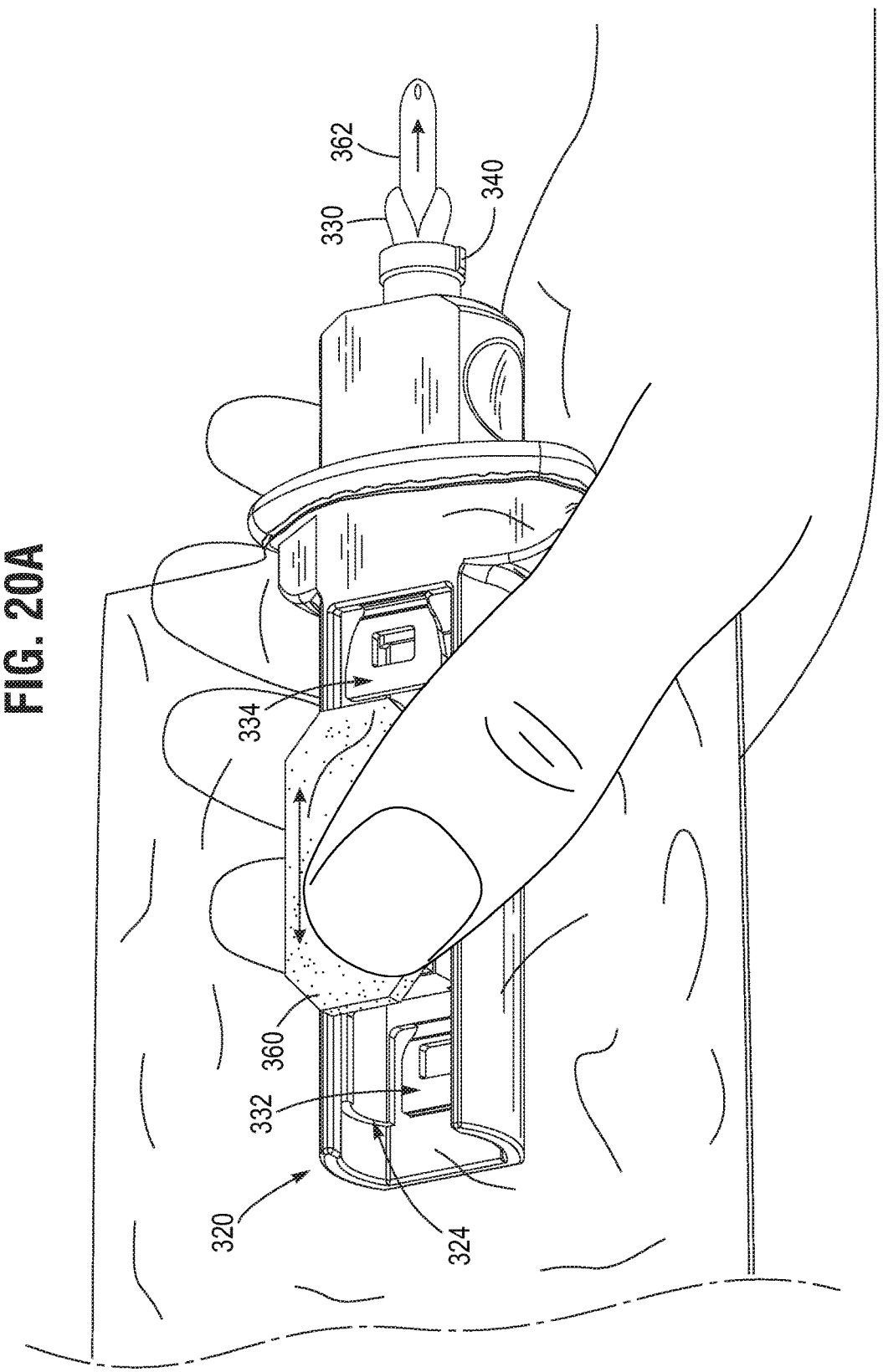

FIGS. 20A-20D are perspective views of the integrated assemblies 320 of FIGS. 19A and 19C mounted to an outer panel of a sterile bag showing a variety of different ways to grasp and reciprocate the finger pad 350 to advance the catheter from within the bag. For instance, FIG. 20A shows a user holding the outlet end of the bag in one hand with the palm and fingers under the integrated assembly 320 and the thumb in contact with the friction-enhancing pad 360. Back-and-forth movement of the thumb on the friction-enhancing pad 360 advances the catheter 362 out of the sterile bag.

FIG. 20B shows a two-handed operation, where the right hand grasps and steadies the integrated assembly 320 while the left hand reciprocates the friction-enhancing pad 360 and underlying finger pad 350. Some users have a difficult time with dexterity, and so the user may contact the wide friction-enhancing pad 360 with the heel of his or her palm.

Figure 20C:
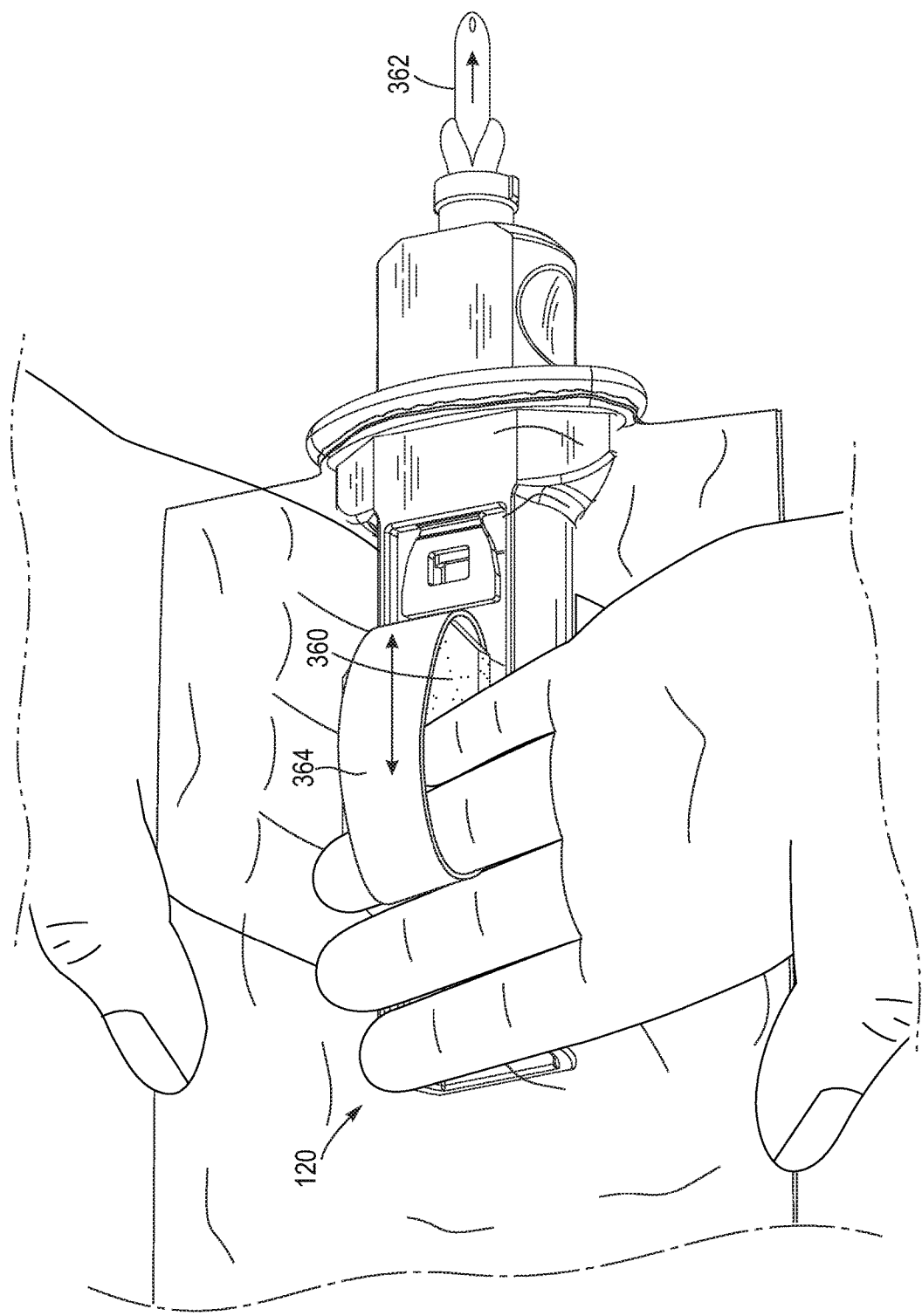

In FIG. 20C the user merely sandwiches the integrated assembly 320 between his or her two hands, without grasping at all. One or more fingers may be inserted through the strap 364 to gain purchase on the finger pad 350 without the need for grasping. Back-and-forth movement of the hand in contact with the friction-enhancing pad 360 and within the strap 364 advances the catheter 362.

Finally, FIG. 20D illustrates a still further possible configuration where the user stabilizes the integrated assembly 320 from underneath with the right hand while manipulating the friction-enhancing pad 360 with the thumb of the left hand through the strap 364. It should be noted again that the generally rectangular lateral cross-section of the integrated assembly 320 aids in these various movements by presenting resistance to rotation about the longitudinal axis and also a flatter profile for the user to compress between his or her hands.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those It is claimed:

1. A closed intermittent urinary catheter system equipped with a catheter dispensing device, comprising:
   a) sterile flexible packaging defining a closed reservoir with an outlet opening;
   b) a catheter defining a longitudinal axis retained within the reservoir and having a distal insertion tip positioned adjacent to and aimed toward the outlet opening;
   c) a first movement control device mounted over the catheter proximally from the distal insertion tip and manually manipulable from outside and through the flexible packaging, the first movement control device having a locking member that moves to an unlocked position upon relative distal movement of the catheter therein to allow relative distal movement of the catheter, and moves to a locked position upon relative proximal movement of the catheter to prevent further relative proximal movement of the catheter;
   d) a second movement control device mounted over the catheter between the distal insertion tip and the first movement control device and being manually manipulable from outside and through the flexible packaging, the second movement control device having a locking member that moves to an unlocked position upon relative distal movement of the catheter therein to allow relative distal movement of the catheter, and moves to a locked position upon relative proximal movement of the catheter to prevent further relative proximal movement of the catheter, wherein
   e) coordinated movement of the first and second movement control devices toward and away from one another causes the catheter to be advanced distally through the outlet opening; and the system further comprises:
   f) a handle grip that includes (i) a hand graspable base member fixedly attached to the second movement control device, and (ii) a movable member reciprocally engaged to the base member and fixedly attached to the first movement control device, wherein reciprocation of the movable member relative to the base member effects the coordinated movement of the first and second movement control devices so as to effect distal advancement of the catheter through the outlet opening.

2. The system of claim 1, wherein the flexible packaging is a plastic bag and the second movement control device is attached to the bag.

3. The system of claim 1, wherein the second movement control device is disposed at and attached to one end of the flexible packaging with a first portion of the second movement control device disposed inside the reservoir and a second portion of the second movement control device disposed outside the reservoir, whereby a passageway through the main body of the second movement control device defines the outlet opening.

4. The system of claim 3, wherein the outlet opening further includes an introducer tip sized to fit within an outer end of a urethra and made of a flexible elastomer which has petals that the catheter spreads apart upon distal passage therethrough.

5. The system of claim 1, wherein:
   a) each movement control device comprises (i) a main body having a passageway defining a central axis, and (ii) the locking member hingedly attached to the main body for pivoting about a pivot axis and having an orifice defining a central axis extending therethrough, (iii) whereby the locking member is pivotable between the unlocked position wherein the central axis of the orifice is aligned with the central axis of the passageway and permits distal movement of the catheter relative to the movement control device, and the locked position wherein the central axis of the orifice is misaligned with the central axis of the passageway and resists proximal movement of the catheter relative to the movement control device, and
   b) the catheter extends through the passageway and the orifice in both of the movement control devices.

6. The system of claim 5, further comprising a release element within the reservoir in operable engagement with the locking member of the first movement control device and manipulable from outside and through the flexible packaging, the release element configured to be actuated and hold the locking members of the first and second movement control devices in their unlocked positions so as to permit free movement of the catheter through the first and second movement control devices.

7. The system of claim 5, wherein the main body of each of the first and second movement control devices has longitudinally spaced opposed first and second ends, and the passageway through the main body extends between an opening in the first end of the main body and an opening in the second end of the main body, and first and second laterally spaced engagement members extend longitudinally from the first end of the main body, the engagement members positioned on diametric sides of the opening in the first end of the main body, and the locking member is hingedly attached at a first lateral end to the first engagement member for pivoting about the pivot axis.

8. The system of claim 1, further including a third movement control device disposed at and attached to one end of the flexible packaging just inside the outlet opening, the third movement control device having a locking member that is biased to a locked position that prevents relative distal movement of the catheter through the third movement control device, and wherein the outlet opening of the flexible packaging has an introducer tip sized to fit within the outer end of the urethra and made of a flexible elastomer which has petals that the catheter spreads apart upon distal passage therethrough, and the packaging is collapsible at the outlet opening so that pressure on the introducer tip from the urethra collapses the packaging and moves the locking member from the locked position to an unlocked position that allows relative distal movement of the catheter through the third movement control device.

9. A closed intermittent urinary catheter system equipped with a catheter dispensing device, comprising:
   a) sterile flexible packaging defining a closed reservoir with an outlet opening;
   b) a catheter defining a longitudinal axis retained within the reservoir and having a distal insertion tip positioned adjacent to and aimed toward the outlet opening;
   c) a first movement control device within the reservoir mounted over the catheter and manually manipulable from outside and through the flexible packaging, the first movement control device configured to permit distal movement of the catheter relative to the first movement control device and automatically resist proximal movement of the catheter relative to the first movement control device; and
   d) a second movement control device within the reservoir mounted over the catheter and being manually graspable from outside the flexible packaging, the second movement control device being fixed with respect to and adjacent the outlet opening and configured to automatically permit distal movement of the catheter relative to the second movement control device and automatically resist proximal movement of the catheter relative to the second movement control device, wherein reciprocal movement of the first movement control device relative to the second movement control device causes the catheter to be advanced distally through the outlet opening, wherein the flexible packaging is a plastic bag and the second movement control device is fixed within a base member attached to the bag, wherein a first portion of the base member is disposed inside the bag and a second portion of the base member is disposed outside the bag, and whereby a passageway through the second portion of the base member defines the outlet opening, and wherein the first movement control device is fixedly mounted within a movable member slidably disposed for reciprocal movement in a distal-proximal direction within a channel in the base member, the movable member including a finger pad facing toward the flexible packaging that is manually manipulable from outside and through the flexible packaging, the finger pad having a flat surface.

10. The system of claim 9, wherein the outlet opening further includes an introducer tip sized to fit within an outer end of a urethra and made of a flexible elastomer which has petals that the catheter spreads apart upon distal passage therethrough.

11. The system of claim 9, wherein the finger pad further includes two laterally-oriented bars on opposite longitudinal ends of the flat surface.

12. The system of claim 9, further including a friction-enhancing pad adhered to an outer surface of the flexible packaging directly outside of the finger pad.

13. The system of claim 12, wherein the friction-enhancing pad is a compressible material.

14. The system of claim 12, wherein the friction-enhancing pad has a double-headed arrow indicator thereon to indicate the distal-proximal reciprocal movement direction of the movable member.

15. The system of claim 9, wherein the finger pad is adhered to the flexible packaging and further including a strap attached outside the flexible packaging directly outside of the finger pad, the strap sized to receive one or more fingers of a user.

16. The system of claim 9, wherein:
a) each movement control device comprises (i) a main body having a passageway defining a central axis, and (ii) the locking member hingedly attached to the main body for pivoting about a pivot axis and having an orifice defining a central axis extending therethrough, (iii) whereby the locking member is pivotable between the unlocked position wherein the central axis of the orifice is aligned with the central axis of the passageway and permits distal movement of the catheter relative to the movement control device, and the locked position wherein the central axis of the orifice is misaligned with the central axis of the passageway and resists proximal movement of the catheter relative to the movement control device, and
b) the catheter extends through the passageway and the orifice in both of the movement control devices.

17. A closed intermittent urinary catheter system equipped with a catheter dispensing device, comprising:
a) sterile flexible packaging defining a closed reservoir with an outlet opening;
b) a catheter defining a longitudinal axis retained within the reservoir and having a distal insertion tip positioned adjacent to and aimed toward the outlet opening;
c) a first movement control device mounted over the catheter proximally from the distal insertion tip and manually manipulable from outside and through the flexible packaging, the first movement control device having a locking member that moves to an unlocked position upon relative distal movement of the catheter therein to allow relative distal movement of the catheter, and moves to a locked position upon relative proximal movement of the catheter to prevent further relative proximal movement of the catheter; and
d) a second movement control device mounted over the catheter between the distal insertion tip and the first movement control device and being manually manipulable from outside and through the flexible packaging, the second movement control device having a locking member that moves to an unlocked position upon relative distal movement of the catheter therein to allow relative distal movement of the catheter, and moves to a locked position upon relative proximal movement of the catheter to prevent further relative proximal movement of the catheter, wherein
e) coordinated movement of the first and second movement control devices toward and away from one another causes the catheter to be advanced distally through the outlet opening,
f) each movement control device comprises (i) a main body having a passageway defining a central axis, and (ii) the locking member hingedly attached to the main body for pivoting about a pivot axis and having an orifice defining a central axis extending therethrough, (iii) whereby the locking member is pivotable between the unlocked position wherein the central axis of the orifice is aligned with the central axis of the passageway and permits distal movement of the catheter relative to the movement control device, and the locked position wherein the central axis of the orifice is misaligned with the central axis of the passageway and resists proximal movement of the catheter relative to the movement control device, and
g) the catheter extends through the passageway and the orifice in both of the movement control devices, and wherein the main body of each of the first and second movement control devices has longitudinally spaced opposed first and second ends, and the passageway through the main body extends between an opening in the first end of the main body and an opening in the second end of the main body, and first and second laterally spaced engagement members extend longitudinally from the first end of the main body, the engagement members positioned on diametric sides of the opening in the first end of the main body, and the locking member is hingedly attached at a first lateral end to the first engagement member for pivoting about the pivot axis.

18. The system of claim 17, further including a handle grip that includes (i) a hand graspable base member fixedly attached to the second movement control device, and (ii) a movable member reciprocally engaged to the base member and fixedly attached to the first movement control device, wherein reciprocation of the movable member relative to the base member effects the coordinated movement of the first and second movement control devices so as to effect distal advancement of the catheter through the outlet opening, the movable member including a finger pad facing toward the flexible packaging that is manually manipulable from outside and through the flexible packaging, and further including a friction-enhancing pad adhered to an outer surface of the flexible packaging directly outside of the finger pad.

19. A closed intermittent urinary catheter system equipped with a catheter dispensing device, comprising:
    a) sterile flexible packaging defining a closed reservoir with an outlet opening;
    b) a catheter defining a longitudinal axis retained within the reservoir and having a distal insertion tip positioned adjacent to and aimed toward the outlet opening;
    c) a first movement control device mounted over the catheter proximally from the distal insertion tip and manually manipulable from outside and through the flexible packaging, the first movement control device having a locking member that moves to an unlocked position upon relative distal movement of the catheter therein to allow relative distal movement of the catheter, and moves to a locked position upon relative proximal movement of the catheter to prevent further relative proximal movement of the catheter; and
    d) a second movement control device mounted over the catheter between the distal insertion tip and the first movement control device and being manually manipulable from outside and through the flexible packaging, the second movement control device having a locking member that moves to an unlocked position upon relative distal movement of the catheter therein to allow relative distal movement of the catheter, and moves to a locked position upon relative proximal movement of the catheter to prevent further relative proximal movement of the catheter, wherein
    e) coordinated movement of the first and second movement control devices toward and away from one another causes the catheter to be advanced distally through the outlet opening, and
    f) further including a third movement control device disposed at and attached to one end of the flexible packaging just inside the outlet opening, the third movement control device having a locking member that is biased to a locked position that prevents relative distal movement of the catheter through the third movement control device, and wherein the outlet opening of the flexible packaging has an introducer tip sized to fit within the outer end of the urethra and made of a flexible elastomer which has petals that the catheter spreads apart upon distal passage therethrough, and the packaging is collapsible at the outlet opening so that pressure on the introducer tip from the urethra collapses the packaging and moves the locking member from the locked position to an unlocked position that allows relative distal movement of the catheter through the third movement control device.

20. The system of claim 19, further including a handle grip that includes (i) a hand graspable base member fixedly attached to the second movement control device, and (ii) a movable member reciprocally engaged to the base member and fixedly attached to the first movement control device, wherein reciprocation of the movable member relative to the base member effects the coordinated movement of the first and second movement control devices so as to effect distal advancement of the catheter through the outlet opening, the movable member including a finger pad facing toward the flexible packaging that is manually manipulable from outside and through the flexible packaging, and further including a friction-enhancing pad adhered to an outer surface of the flexible packaging directly outside of the finger pad.

* * * * *